(12) United States Patent
Michnick et al.

(10) Patent No.: US 8,101,364 B2
(45) Date of Patent: *Jan. 24, 2012

(54) FRAGMENTS OF FLUORESCENT PROTEINS FOR PROTEIN FRAGMENT COMPLEMENTATION ASSAYS

(75) Inventors: Stephen William Watson Michnick, Westmount (CA); Marnie L. MacDonald, Pleasanton, CA (US); Jane Lamerdin, Livermore, CA (US)

(73) Assignee: Odyssey Thera, Inc., San Ramon, CA (US)

( * ) Notice: Subject to any disclaimer, the term of this patent is extended or adjusted under 35 U.S.C. 154(b) by 1077 days.

This patent is subject to a terminal disclaimer.

(21) Appl. No.: 11/656,543

(22) Filed: Jan. 23, 2007

(65) Prior Publication Data

US 2007/0254373 A1    Nov. 1, 2007

Related U.S. Application Data

(63) Continuation of application No. 10/724,178, filed on Dec. 1, 2003, now Pat. No. 7,166,424, and a continuation-in-part of application No. 10/353,090, filed on Jan. 29, 2003, now Pat. No. 7,160,691, which is a continuation of application No. 10/154,758, filed on May 24, 2002, now Pat. No. 6,929,916, which is a continuation of application No. 09/499,464, filed on Feb. 7, 2000, now Pat. No. 6,428,951, which is a continuation of application No. 09/017,412, filed on Feb. 2, 1998, now Pat. No. 6,270,964.

(60) Provisional application No. 60/461,133, filed on Apr. 9, 2003.

(51) Int. Cl.
*G01N 33/53* (2006.01)

(52) U.S. Cl. ............................... 435/7.1; 435/7.2; 435/86
(58) Field of Classification Search ....................... None
See application file for complete search history.

(56) References Cited

U.S. PATENT DOCUMENTS 6,780,599 B2 * 8/2004 Hamilton et al. .............. 435/7.1

OTHER PUBLICATIONS

Evangelista et al. (Cell Biology 1996 vol. 6, p. 196-199).*

* cited by examiner

*Primary Examiner* — Jacob Cheu
(74) *Attorney, Agent, or Firm* — Issac A. Angres

(57) ABSTRACT

The present invention is directed to Protein-fragment Complementation Assays (PCAs) and assay compositions based on fluorescent proteins. The invention provides methods for fragmenting fluorescent proteins and generating mutant fragments with desired spectral characteristics for PCA. The invention encompasses assays and compositions based on fluorescent proteins from the species *Aequorea*, *Anemonia* and *Anthozoa*. In particular, the invention is directed to fragments of mutant fluorescent proteins having improved spectral properties over the wild-type proteins. The invention encompasses fragments of mutant versions of *A. Victoria* green fluorescent protein (GFP), in particular yellow fluorescent proteins (EYFP and super-EYFP), 'Venus', cyan, 'citrine', blue, cyan-green, and photoactivatable variants of GFP The invention also encompasses red fluorescent PCAs based on Discosoma red fluorescent protein (RFP PCA) and a kindling fluorescent protein PCA (KFP1 PCA) derived from *Anemonia sulcata*. Any useful mutation of a fluorescent protein can be engineered into a fragment, generating a wide range of assays useful for drug discovery, target validation, high-throughput screening, high-content screening, pathway mapping, drug mechanism-of-action studies, biosensors, and diagnostics.

17 Claims, 12 Drawing Sheets

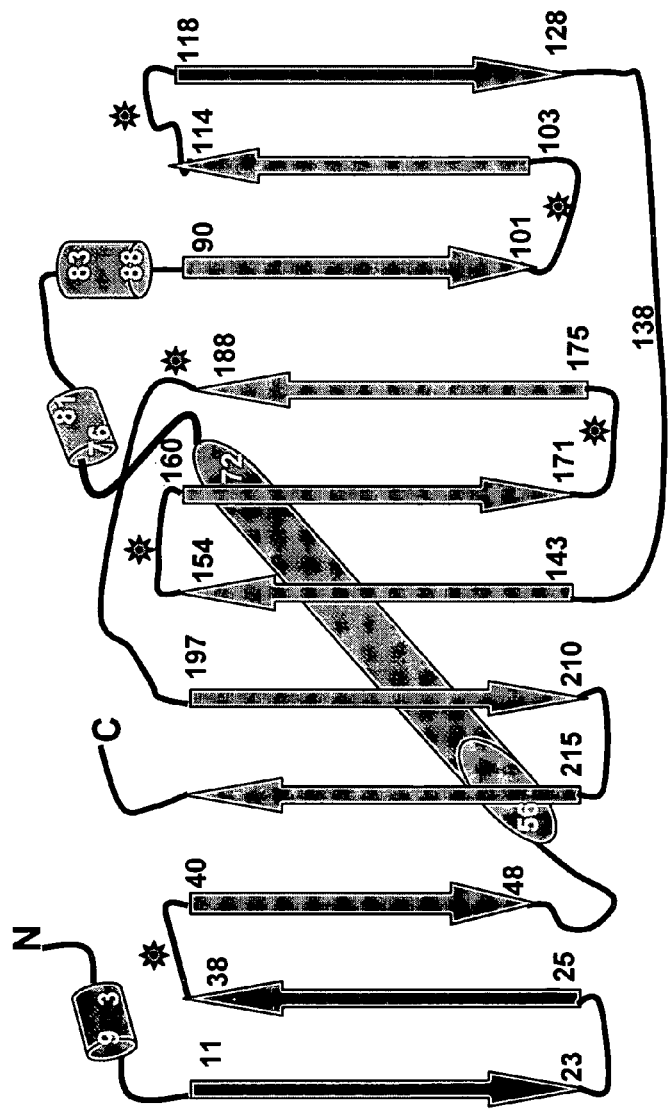

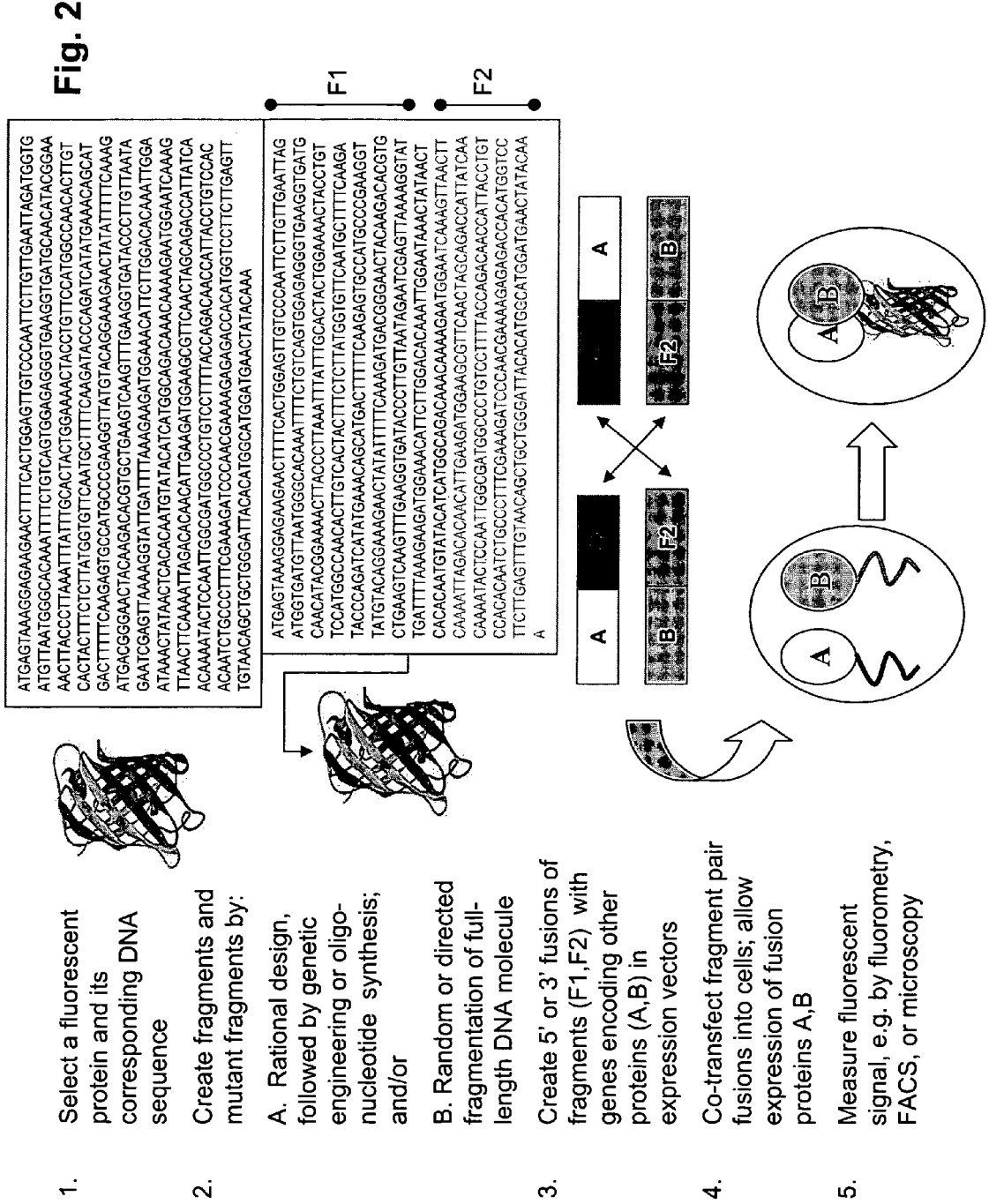

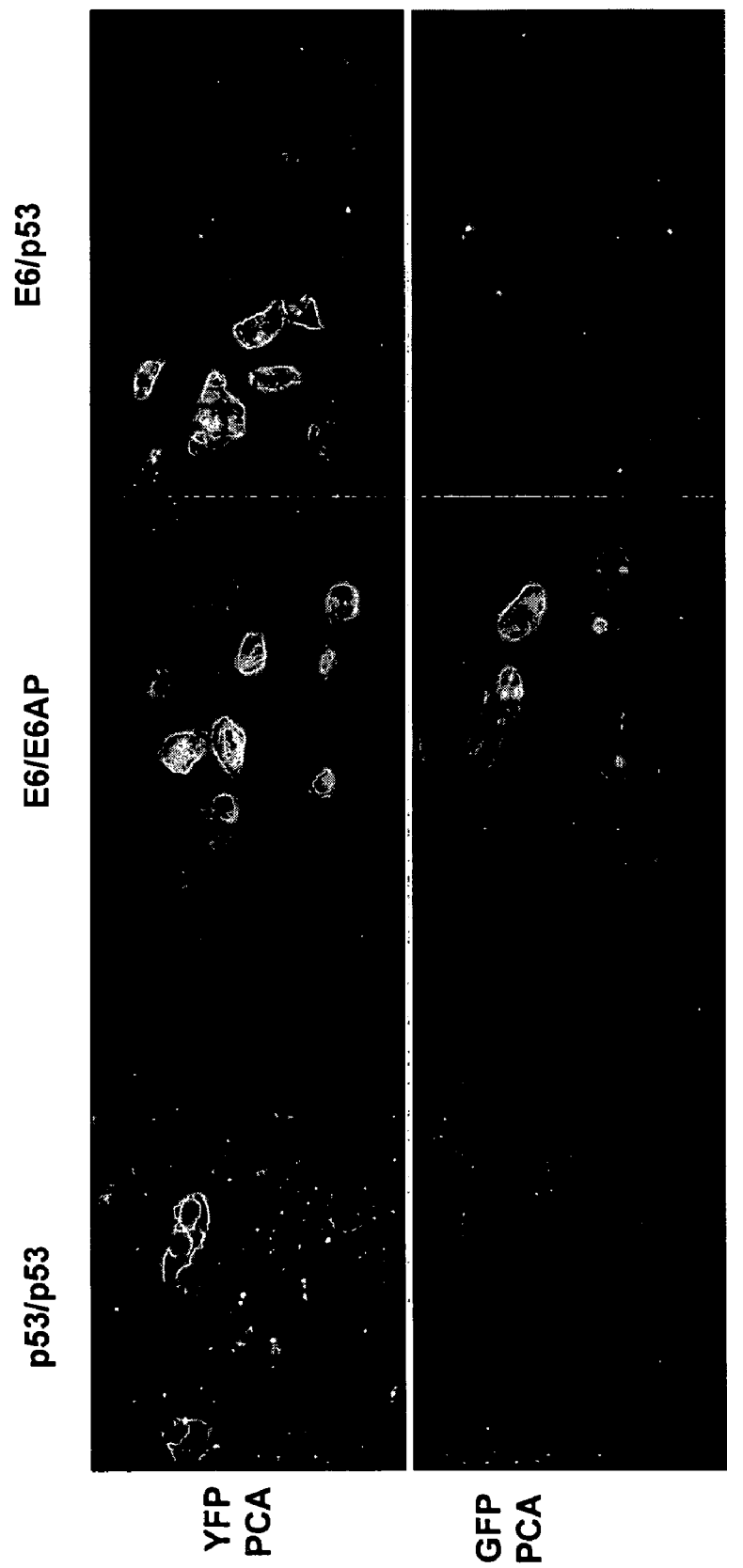

Examples of PCAs based on alternative fragmentation sites of YFP

Fig. 6
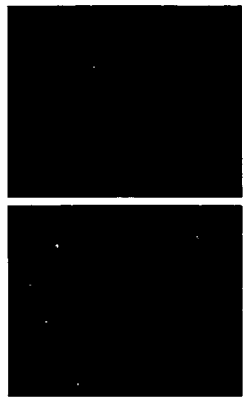
c. Single fragment control:
Pdk2-YFP[1] (F64L/S65G/V68L/S72A)
d. Single fragment control:
Pdk2-YFP[2] (T203Y)
*Note: amino acid changes are designated relative to wild-type GFP*
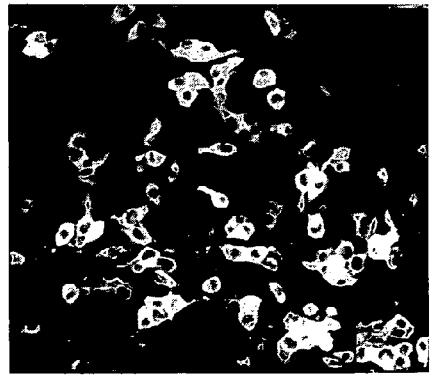
a. MEK-SEYFP[1] (F64L/S65G/V68L/S72A/M153T)*
ERK-YFP[2]-T203Y*
b. MEK-YFP[1] (S65G/V68L/S72A*)
ERK-YFP[2] (T203Y*)

An intense fluorescent PCA (IFP PCA) based on mutant fragments of YFP

Enhanced PCA signals based on mutant fragments:
IFP (SEYFP-F46L) versus EYFP

High-content assays based on IFP PCA:
cytokine-dependent translocation of p65/p50

Spectrally shifted (blue) PCAs based on mutant fluorescent protein fragments
(excitation= 436 nm, emission= 480 nm)

Multi-color protein-fragment complementation assays (PCA)

FRAGMENTS OF FLUORESCENT PROTEINS FOR PROTEIN FRAGMENT COMPLEMENTATION ASSAYS

This application is a continuation of U.S. application Ser. No. 10/724,178 filed Dec. 1, 2003, and now U.S. Pat. No. 7,166,424. This application claims the priority benefit under 35 U.S.C. section 119 of U.S. Provisional Patent Application No. 60/461,133 entitled "Fragments of Fluorescent Proteins for Protein Fragment Complementation Assays", filed Apr. 9, 2003, which is in its entirety herein incorporated by reference. This Application is also a continuation-in-part of U.S. application Ser. No. 10/353,090 filed Jan. 29, 2003; now U.S. Pat. No. 7,160,691; which application is a continuation of U.S. application Ser. No. 10/154,758 filed May 24, 2002; now U.S. Pat. No. 6,929,916; which is a continuation of U.S. Ser. No. 09/499,464 filed Feb. 7, 2000; and now U.S. Pat. No. 6,428,951; which is a continuation of U.S. Ser. No. 09/017,412 filed Feb. 2, 1998; and now U.S. Pat. No. 6,270,964.

BACKGROUND OF THE INVENTION

This invention relates generally to the fields of biology, molecular biology, chemistry and biochemistry. Specifically, the invention is directed to protein-fragment complementation assays (PCAs) based on fluorescent proteins. This invention is directed to methods for the design and creation of suitable fragment pairs, to the compositions of the fragments, and to combinations suitable for PCA. Preferred embodiments include fragments of mutant fluorescent proteins having properties suitable for biotechnology applications.

The growing list of naturally fluorescent, bioluminescent or phosphorescent proteins includes GFP derived from *Aequorea Victoria*, and a growing number of sequence variants of GFP with useful properties. The list also includes the red fluorescent protein (RFP) derived from Discosoma; and the kindling fluorescent protein (KFP1) derived from Anemonia. These proteins are autocatalytic enzymes that are all capable of generating highly visible, efficiently emitting internal fluorophores as a result of endo-cyclization of core amino acid residues. Another common feature of the fluorescent proteins is that the signal is stable, species independent, and does not require any substrates or cofactors for the generation of a signal. These fluorescent proteins are remarkably similar structurally allowing similar principles of protein engineering to be applied across species.

The full-length DNA, and corresponding amino acid sequence of one isotype of GFP ("wild-type GFP") is shown in TABLE 1 and has been fully described and characterized (see e.g. Tsien et al., 1998, Ann. Rev. Biochem. 67: 509-44). The intact protein (FIGS. 1 and 2B) generates a strong visible absorbance and fluorescence from a p-hydroxybenzylidene-imidazolone chromophore, which is generated by cyclization and oxidation of the protein's own Ser-Tyr-Gly sequence at positions 65 to 67. Newly synthesized fluorescent protein polypeptides need to mature properly before emitting fluorescence. The maturation process involves two steps: folding and chromophore formation. First, the protein folds into a native conformation, and then the internal tripeptide cyclizes and is oxidized. In this regard the fluorescent protein is an enzyme which autocatalyzes the cyclization reaction, requiring only molecular oxygen for completion of the reaction.

A variety of useful mutant versions of the full-length, wild-type GFP have been generated and have been termed '*Aequorea* fluorescent protein (AFP) variants' or AFPs. These "mutant fluorescent proteins" have proven to have wide applicability for biology and biotechnology applications as a result of their improved spectral properties. Some of the reported GFP variants are shown in Table 2. By conventional usage, the positions of the mutations (as in Table 2 and throughout this invention) are denoted relative to the sequence of wild-type GFP (Table 1). Many of these AFPs exhibit vastly improved properties over the original wild-type GFP in terms of signal intensity, generating a fluorescence signal 5 to 30 times that of the wild-type protein. The enhanced GFP (EGFP), which is the basis for nearly all biology applications and for mutant fluorescent proteins, has improved codon usage for mammalian cells.

Starting with GFP, mutations at the site of the chromophore have been created which result in different color variants. Mutations of the side chains in contact with the chromophore have been shown to further enhance protein folding and brightness. Combinations of mutations have been created that have spectral shifts and that fold more rapidly at 37° C., producing brighter signals for cell biology applications. The most common spectral variants include the widely-used yellow (YFP/EYFP), cyan (CFP/ECFP) and BFP variants (R. Y. Tsien, 1998, "The Green Fluorescent Protein", in: Annual Reviews of Biochemistry 67: 509-544).

Additional mutants of GFP have been created with unique properties. These include a 'CGFP' variant with an excitation and emission wavelength intermediate between CFP and EGFP (J. Zhang et al., 2000, "Creating new fluorescent probes for cell biology", Nature Reviews 3: 906-918). The 'citrine' variant of YFP (YFP-Q69M) confers a lower pKa than for previous YFPs, indifference to chloride anion, twice the photostability of previous YFPs, and much better expression at 37C and in organelles (O. Griesbeck et al., 2001, "Reducing the Environmental Sensitivity of Yellow Fluorescent Protein", J. Biol. Chem 276: 29188-29194).

Several versions of YFP have been created using random mutagenesis. These mutant proteins have fluorescence intensities 3-30 times brighter than EYFP. They include the so-called super-EYFP (SEYFP) (EYFP-F64L/M153T/V163A/S175G) and 'Venus' (SEYFP-F46L) (T. Nagai et al., 2002, "A variant of yellow fluorescent protein with fast and efficient maturation for cell-biological applications", Nature Biotech. 20: 87-90). Venus contains the novel mutation, F46L, which at 37° C. greatly accelerates oxidation of the chromophore, the rate-limiting step of mutation. As a result of the additional SEYFP mutations, Venus SEYFP-F46L also folds well and is relatively tolerant of exposure to acidic or high chloride anion concentrations.

A photoactivatable form of GFP named PA-GFP (GFP-V163A/T203H) has been reported that, after intense irradiation with 413-nm light, increases fluorescence 100 times when excited by 488-nm light and remains stable for days under aerobic conditions (G. H. Patterson & J. L.-Schwartz, "A photoactivatable GFP for selective photolabeling of proteins and cells", Science 297: 1873-1877, 2002).

TABLE 1

Full-length *Aequorea* GFP nucleic acid sequence (716 bp) (SEQ ID No: 1) and corresponding amino acid sequence (238 aa) (SEQ ID No: 2). Amino acids are numbered at every 5th position. This sequence is for the wild-type protein. In "enhanced" versions of GFP (EGFP, EYFP, ECFP) a valine residue is inserted after the initiating methionine. The valine becomes amino acid # 2 and the remaining amino acids are shifted accordingly. Descriptions of GFP mutants (as in Table 2 and throughout the specifications) refer to the numbering shown below. Alternative fragmentation sites that are the subject of the present invention are shown at the following regions (underlined): amino acid residues 38-40 (region 1); residues 101-103 (region 2); residues 114-118 (region 3); residues 154-160 (region 4); residues 171-175 (region 5); and residues 188-190 (region 6). The positions of specific amino acid residues are shown for Tyrosine 39 (Y39), Aspartate 102 (D102), Glutamine 157 (Q157), Lysine 158 (K158), Aspartate 173 (D173) and Aspartate 190 (D190)

```
atg agt aaa gga gaa gaa ctt ttc act gga gtt gtc cca att ctt gtt
Met Ser Lys Gly Glu Glu Leu Phe Thr Gly Val Val Pro Ile Leu Val
1               5                   10                  15 gaa tta gat ggt gat gtt aat ggg cac aaa ttt tct gtc agt gga gag
Glu Leu Asp Gly Asp Val Asn Gly His Lys Phe Ser Val Ser Gly Glu
            20                  25                  30 ggt gaa ggt gat gca aca tac gga aaa ctt acc ctt aaa ttt att tgc
Gly Glu Gly Asp Ala Thr Tyr Gly Lys Leu Thr Leu Lys Phe Ile Cys
        35              Y39 40              45 act act gga aaa cta cct gtt cca tgg cca aca ctt gtc act act ttc
Thr Thr Gly Lys Leu Pro Val Pro Trp Pro Thr Leu Val Thr Thr Phe
    50                  55                  60 tct tat ggt gtt caa tgc ttt tca aga tac cca gat cat atg aaa cgg
Ser Tyr Gly Val Gln Cys Phe Ser Arg Tyr Pro Asp His Met Lys Arg
65              70                  75                  80 cat gac ttt ttc aag agt gcc atg ccc gaa ggt tat gta cag gaa aga
His Asp Phe Phe Lys Ser Ala Met Pro Glu Gly Tyr val Gln Glu Arg
            85                  90                  95 act ata ttt ttc aaa gat gac ggg aac tac aag aca cgt gct gaa gtc
Thr Ile Phe Phe Lys Asp Asp Gly Asn Tyr Lys Thr Arg Ala Glu Val
            100     D102        105                 110 aag ttt gaa ggt gat acc ctt gtt aat aga atc gag tta aaa ggt att
Lys Phe Glu Gly Asp Thr Leu Val Asn Arg Ile Glu Leu Lys Gly Ile
    115 G116            120                 125 gat ttt aaa gaa gat gga aac att ctt gga cac aaa ttg gaa tac aac
Asp Phe Lys Glu Asp Gly Asn Ile Leu Gly His Lys Leu Glu Tyr Asn
    130                 135                 140 tat aac tca cac aat gta tac atc atg gca gac aaa caa aag aat gga
Tyr Asn Ser His Asn Val Tyr Ile Met Ala Asp Lys Gln Lys Asn Gly
145                 150                 155     Q157 K158    160 atc aaa gtt aac ttc aaa att aga cac aac att gaa gat gga agc gtt
Ile Lys Val Asn Phe Lys Ile Arg His Asn Ile Glu Asp Gly Ser Val
            165                 170     D173        175 caa cta gca gac cat tat caa caa aat act cca att ggc gat ggc cct
Gln Leu Ala Asp His Tyr Gln Gln Asn Thr Pro Ile Gly Asp Gly Pro
            180                 185         D190 gtc ctt tta cca gac aac cat tac ctg tcc aca caa tct gcc ctt tcg
Val Leu Leu Pro Asp Asn His Tyr Leu Ser Thr Gln Ser Ala Leu Ser
            195                 200                 205 aaa gat ccc aac gaa aag aga gac cac atg gtc ctt ctt gag ttt gta
Lys Asp Pro Asn Glu Lys Arg Asp His Met Val Leu Leu Glu Phe Val
            210                 215                 220 aca gct gct ggg att aca cat ggc atg gat gaa cta tac aaa
Thr Ala Ala Gly Ile Thr His Gly Met Asp Glu Leu Tyr Lys
225                 230                 235
```

TABLE 2

Spectral characteristics of the major classes of Aequorea fluorecent proteins (AFPs)

| Mutation | Common name | $\lambda_{exc}(\epsilon)$ | $\lambda_{em}$(QY) | Rel. fl. @ 37° C. |
|---|---|---|---|---|
| Class 1, wild-type | | | | |
| None or Q80R | Wild type | 395-397 (25-30) 470-475 (9.5-14) | 504 (0.79) | 6 |
| F99S, M153T, V163A | Cycle 3 | 397 (30) 475 (6.5-8.5) | 506 (0.79) | 100 |
| Class 2, phenolate anion | | | | |
| S65T | | 489 (52-58) | 509-511 (0.64) | 12 |
| F64L, S65T | EGFP | 488 (55-57) | 507-509 (0.60) | 20 |
| F64L, S65T, V163A | | 488 (42) | 511 (0.58) | 54 |
| S65T, S72A, N149K, M153T, I167T | Emerald | 487 (57.5) | 509 (0.68) | 100 |
| Class 3, neutral phenol | | | | |
| S202F, T203I | H9 | 399 (20) | 511 (0.60) | 13 |
| T203I, S72A, Y145F | H9-40 | 399 (29) | 511 (0.64) | 100 |
| Class 4, phenolate anion with stacked π-electron system (yellow fluorescent proteins) (YFPs) | | | | |
| S65G, S72A, T203F | | 512 (65.5) | 522 (0.70) | 6 |
| S65G, S72A, T203Y | EYFP | 508 (48.5) | 518 (0.78) | 12 |
| S65G, V68L, Q69K, S72A, T203Y | 10C Q69K | 516 (62) | 529 (0.71) | 50 |
| S65G, V58L, S72A, T203Y | 10C | 514 (83.4) | 527 (0.61) | 58 |
| S65G, S72A, K79R, T203Y | Topaz | 514 (94.5) | 527 (0.60) | 100 |
| F46L | EYFP-F46L | 515 (78.7) | 528 (0.61) | ND |
| F64L, M153T, V163A, S175G | SEYFP | 515 (101) | 528 (0.56) | ND |
| F46L, F64L, M153T, V163A, S175G | SEYFP-F46L ('Venus') | see: Nagai et al., Nature Biotech. 20: 87-90, 2002 | | |
| V68L, Q69M | 'Citrine' | see: Griesbeck et al., J. Biol. Chem 276: 29188-29194 (2001) | | |
| V163A, T203H | PA-GFP | see: Patterson et al., Science 297: 1873-1877, 2002 | | |
| Class 5, indole in chromophore (cyan fluorescent proteins) (CFPs) | | | | |
| Y66W | | 436 | 485 | — |
| Y66W, N146I, M153T, V163A | W7 | 434 (23.9) 452 | 476(0.42) 505 | 61 |
| F64L, S65T, Y66W, N146I, M153T, V163A | W1B or ECFP | 434 (32.5) 452 | 476(0.4) 505 | 80 |
| S65A, Y66W, S72A, N146I, M153T, V163A | W1C | 435 (21.2) | 495(0.39) | 100 |
| T203Y | CGFP | see: Sawano & Miyawaki, Nucleic Acid Res. 28: E78 (2000) | | |
| Class 6, imidazole in chromophore (blue fluorescent proteins) (BFPs) | | | | |
| Y66H | BFP | 384 (21) | 448 (0.24) | 18 |
| Y66H, Y145F | P4-3 | 382 (22.3) | 446 (0.3) | 52 |
| F64L, Y66H, Y145F | EBFP | 380-383 (26.3-31) | 440-447 (0.17-0.26) | 100 |
| Class 7, phenyl in chromophore | | | | |
| Y66F | | 360 | 442 | — |

TABLE 3

Alignment of wild type *Aequorea victoria* GFP and *Aequorea*-derived fluorescent proteins (Zhang et al. 2002). New variants of green fluorescent protein (GFP) (SEQ ID No: 2) that encode proteins with altered excitation and emission wavelength properties relative to wild type GFP are aligned. These include the mammalian codon-usage optimized ECFP (cyan) (SEQ ID No: 8), EGFP (green) (SEQ ID No: 3), (cyan), EGFP (green), and EYFP (yellow) (SEQ ID No: 4) variants. Three more recent variants of EYFP include EYFP-Q69M (Citrine) (SEQ ID No: 5), super-EYFP (SEYFP) (SEQ ID No: 6), and SEYFP-F46L ('Venus') (SEQ ID No: 7).

```
GFP       1 -MSKGEELFTGVVPILVELDGDVNGHKFSVSGEGEGDATYGKLTLKFICTTGKLPVPWPT
EGFP      1  MV..........................................................
EYFP      1  MV..........................................................
EYFP-Q69M 1  MV..........................................................
```

TABLE 3-continued

Alignment of wild type Aequorea victoria GFP and Aequorea-derived fluorescent proteins (Zhang et al. 2002). New variants of green fluorescent protein (GFP) (SEQ ID No: 2) that encode proteins with altered excitation and emission wavelength properties relative to wild type GFP are aligned. These include the mammalian codon-usage optimized ECFP (cyan) (SEQ ID No: 8), EGFP (green) (SEQ ID No: 3), (cyan), EGFP (green), and EYFP (yellow) (SEQ ID No: 4) variants. Three more recent variants of EYFP include EYFP-Q69M (Citrine) (SEQ ID No: 5), super-EYFP (SEYFP) (SEQ ID No: 6), and SEYFP-F46L ('Venus') (SEQ ID No: 7).

```
SEYFP       1  MV...................................................
SEYFP-F46L  1  MV..............................................L......
ECFP        1  MV...................................................

GFP        60  LVTTFSYGVQCFSRYPDHMKQHDFFKSAMPEGYVQERTIFFKDDGNYKTRAEVKFEGDTL
EGFP       61  ....LT......................................................
EYFP       61  .....G..L...A................................................
EYFP-Q69M  61  .....G..LM..A................................................
SEYFP      61  ....LG..L...A................................................
SEYFP-F46L 61  ....LG..L...A................................................
ECFP       61  ....LTW......................................................

GFP       120  VNRIELKGIDFKEDGNILGHKLEYNYNSHNVYIMADKQKNGIKVNFKIRHNIEDGSVQLA
EGFP      121  .............................................................
EYFP      121  .............................................................
EYFP-Q69M 121  .............................................................
SEYFP     121  ................................T........A............G....
SEYFP-F46L 121 ................................T........A............G....
ECFP      121  ...............................I......T.........A...........

GFP       180  DHYQQNTPIGDGPVLLPDNHYLSTQSALSKDPNEKRDHMVLLEFVTAAGITHGMDELYK
EGFP      181  ..........................................L.......
EYFP      181  .....................Y....................L.......
EYFP-Q69M 181  .....................Y....................L.......
SEYFP     181  .....................Y....................L.......
SEYFP-F46L 181 .....................Y....................L.......
ECFP      181  ...........................................L.......
```

Fluorescent proteins from species other than *Aequorea victoria* have also been isolated and characterized. The growing list includes a green fluorescent protein from *Renilla reniformis*, and a number of fluorescent proteins from the coral *Anthozoa*. These include the red fluorescent protein from Discosoma (DsRed) (M. V. Matz et al., 1999, Nature Biotech. 17:969-973) which has been crystallized (Yarbrough et al., 2001, Proc. Natl. Acad. Sci. 98: 462-467) and has found wide applicability as a biology tool. Although the coral fluorescent proteins have only 26-30% sequence identity with *Aequorea* GFP, they are remarkably similar structurally. In particular, the coral fluorescent proteins share the same β-can fold first observed in GFP. All the key secondary structure elements observed in GFP could be easily detected in the coral proteins in the same arrangements, and remarkable similarity was observed in the stretches forming the "caps' of the can. Key residues thought to be involved in chromophore formation in GFP are also conserved in the coral proteins, including an Arginine at residue 96, the Tyrosine at residue 66 and Glycine at residue 67.

The structural homology of fluorescent proteins among various species means that many of the principles of genetic engineering and protein engineering previously applied to GFP can also be applied to these fluorescent proteins to create variants with desirable properties for biological applications and biotechnology.

The availability of a bright orange-red fluorescent protein with a high quantum yield would be particularly useful for biological studies as it is spectrally distinct from the previously described green, yellow and cyan variants of GFP. DrFP583, commonly known as DsRed, is a 28-kDa polypeptide that has essentially the same chromophore as GFP, which is auto-catalytically formed from an internal Gln-Tyr-Gly (residues 66-68) tripeptide. DsRed is remarkably similar structurally to *A. victoria* GFP. In fact, the overall fold of DsRed is virtually identical to GFP, consisting of a slightly irregular 11-stranded beta-barrel (described as a beta can) with a coaxial central helix and alpha-helical caps on the barrel ends. The sequence alignment of the coral fluorescent proteins with *Aequorea* GFP is shown in Table 4.

A number of mutant versions of DsRed have now been described with faster rates of chromophore maturation than the wild-type protein (B. J. Bevis and B. S. Glick, Nature Biotech. 20: 83-86, 2002). Importantly, DsRed has recently been engineered into a monomeric form (mRFP) (R. E. Campbell et al., Jun. 11, 2002, "A monomeric red fluorescent protein", Proc. Natl. Acad. Sci. 99(12): 7877-7882) which is more useful than the multimeric protein as a reporter. mRFP1 is a monomer, the signal matures >10-fold faster than for DsRed, and the monomeric protein has minimal emission at wavelengths suitable for excitation of GFP.

A unique GFP-like chromoprotein asCP from the sea anemone *Anemonia sulcata* was recently discovered (Chudakov, D. M., et al. 2003, Kindling fluorescent proteins for precise in vivo photolabeling". Nat. Biotechnol. 21, 191-194). asCP is initially nonfluorescent, but in response to intense green light irradiation it becomes brightly fluorescent (kindles) with emission at 595 nm. Kindled asCP relaxes back to the initial nonfluorescent state with a half-life of <10 seconds. Alternatively, fluorescence can be "quenched" instantly and completely by a brief irradiation with blue light. A mutant (asCP A148G, or KFP1) has been generated which is capable of unique irreversible photoconversion from the nonfluorescent to a stable bright-red fluorescent form that has 30 times greater fluorescent intensity than the unkindled protein. This "kindling fluorescent protein" can be used for precise in vivo photolabeling to track the movement of cells, organelles and proteins.

Fluorescent proteins have proven to be useful reporters for monitoring gene expression and protein localization in vivo and in real time (J. M. Tavare et al., 2001, J. Endocrinol. 170: 297-306; Thastrup et al., U.S. Pat. No. 6,518,021). Such assays measure cellular events linked to individual proteins, as compared with binary or higher-order events. A number of other useful applications of fluorescent proteins have been described, including the construction of biochemical sensors and the creation of innovative fusion constructs to analyze protein dynamics in living cells. For the measurement of bimolecular events, FRET (fluorescence resonance energy transfer) or BRET (bioluminescence resonance energy transfer) assays have been well described (A. Miyawaki & R. Tsien, 2000, Methods in Enzymology 327: 472-500; G. W. Gordon et al., 1998, Biophys. J. 74: 2702-2713). GFP, BFP, CFP and RFP have been used in FRET or BRET assays to detect protein-protein interactions, monitor protease activity, and create calcium indicators, among other uses.

It is important to note that all the above-mentioned applications rely upon tagging of proteins of interest with a functional, full-length (or substantially full-length) fluorescent protein (lumiphore). None of the references cited above describe compositions or uses of fragments of fluorescent proteins.

Protein-fragment complementation assays (PCA) represent a general method for the construction of assays for the detection and quantitation of biomolecular and drug interactions (J. N. Pelletier, J. N., Remy, I. and Michnick, S. W. 1998, Protein-Fragment complementation Assays: a general strategy for the in vivo detection of Protein-Protein Interactions, J. Biomolecular Techniques 10:32-19; Remy, I., Pelletier, J. N., Galarneau, A. & Michnick, S. W. 2002, Protein Interactions and Library Screening with Protein Fragment Complementation Strategies, in: Protein-protein Interactions: A Molecular Cloning Manual, Cold Spring Harbor Laboratory Press Chapter 25, 449-475; Michnick, S. W., Remy, I., C.-Valois, F. X., Vallee-Belisle, A., Galarneau, A. & Pelletier, J. N., 2000, Detection of Protein-Protein Interactions by Protein Fragment Complementation Strategies, Parts A and B, in: Methods in Enzymology 328:208-230.; J. N. Pelletier & S. W. Michnick., 1997, A Strategy for Detecting Protein-Protein Interactions in vivo Based on Protein Fragment Complementation. *Protein Engineering*, 10 (Suppl.): 89.).

PCA involves the oligomerization-assisted complementation of fragments of a reporter protein such as a monomeric enzyme, a fluorescent protein, luminescent protein or phosphorescent protein. Dimeric and multimeric enzymes can also be used in PCA, however, monomeric proteins are preferred. As described by Michnick et al. (U.S. Pat. No. 6,270, 964) the ideal properties of a protein suitable for PCA are: 1) a protein or enzyme that is relatively small and monomeric; 2) for which there is a large literature of structural and functional information; 3) for which simple assays exist for the reconstitution of the protein or activity of the enzyme; and 4) for which overexpression in eukaryotic and prokaryotic cells has been demonstrated.

FIG. 1 of U.S. Pat. No. 6,270,964 shows a general description of a PCA. The gene for a protein or enzyme is rationally dissected into two or more fragments. Using molecular biology techniques, the chosen fragments are subcloned, and to the 5' ends of each, proteins that either are known or thought to interact are fused. Co-transfection or transformation of these DNA constructs into cells is then carried out. Reassembly of the probe protein or enzyme from its fragments is catalyzed by the binding of the test proteins to each other, and reconstitution is observed with some assay. It is crucial to understand that these assays will only work if the fused, interacting proteins catalyze the reassembly of the protein or enzyme. That is, observation of reconstituted protein or enzyme activity must be a measure of the interaction of the fused proteins.

U.S. Pat. No. 6,270,964 taught the principles, methods and applications of PCAs for a large number of useful reporters that can generate a fluorescent signal (see Table 1). Example 3 of that patent describes various embodiments of PCAs including a number of specific reporters suitable for PCA. Details were described for glutathione-S-transferase, firefly luciferase, xanthine-guanine phosphoribosyl transferase (XPRT), diaphorase, adenosine deaminase, bleomycin binding protein, hygromycin-B-phosphotransferase, histidinol NAD+oxidoreductase and *Aequorea* green fluorescent protein (GFP). Table 1 of U.S. Pat. No. 6,270,964 described an even larger list of other reporters meeting the criteria for PCA.

In Example 3 of U.S. Pat. No. 6,270,964 a PCA based on GFP was described including its properties and advantages: "GFP from *Aequorea victoria* is becoming one of the most popular protein markers for gene expression. This is because the small, monomeric 238 amino acids protein is intrinsically fluorescent due to the presence of an internal chromophore that results from the autocatalytic cyclization of the polypeptide backbone between residues Ser65 and Gly67 and oxidation of the bond of Tyr 66. The GFP chromophore absorbs light optimally at 395 nm and possesses also a second absorption maximum at 470 nm. This bi-specific absorption suggests the existence of two low energy conformers of the chromophore whose relative population depends on the local environment of the chromophore. A mutant Ser65Thr that eliminates isomerization results in a 4 to 6 times more intense fluorescence than the wild type. Recently the structure of GFP has been solved by two groups, making it a candidate for a structure-based PCA design which we have begun to develop. As with the GST assay we are doing all of our initial development in *E. Coli* with GCN4 leucine zipper-forming sequences as oligomerization domains. Direct detection of fluorescence by visual observation under broad spectrum UV light will be used. We will also test this system in COS cells, selecting for co-transfectants using fluorescence activated cell sorting." The issued claims of U.S. Pat. No. 6,270,964, U.S. Pat. No. 6,294,330 and U.S. Pat. No. 6,428,951 include fluorescent proteins in addition to other reporter classes. PCAs have been used to screen diverse peptide libraries (J. N. Pelletier, et al., 2000, Nature Biotech. 17: 683-690) and cDNA or antibody libraries (E. Moessner et al., 2001, J. Mol. Biol. 308: 115-122; I. Remy et al., submitted for publication); to quantify the association constants of protein domains such as parallel and anti-parallel leucine zipper-forming sequences (K. M. Arndt et al., 2000, J. Mol. Biol. 295: 627-639; I. Ghosh et al., 2000, J. Am. Chem. Soc 122:5658-5659); to detect the drug-induced association and dissociation of protein complexes (I. Remy and S. W. Michnick, 1999, Proc Natl Acad Sci USA 96: 5394-5399); to measure the ligand-induced activation of cellular receptors (I. Remy et al., 1999, Science 283: 990-993); to study transcription factor complexes in live cells (R. Subramaniam et al., 2001, Nature Biotech. 19: 769-772, 2001); to quantitate elements of signal transduction pathways in real time (I. Remy and S. W. Michnick, 2001, Proc Natl Acad Sci USA, 98: 7678-7683, 2001; A. Galarneau et al., 2002, Nature Biotech. 20: 619-622); and to pinpoint the subcellular locations of protein-protein complexes (I. Remy and S. W. Michnick, 2001, Proc Natl Acad Sci USA 98: 7678-

7683; R. Subramaniam et al., 2001, Nature Biotech., 19: 769-772; C.-D. Hu et al., Molecular Cell 9: 789-798, 2002; H. Yu et al., submitted for publication).

Subsequent to our inventions describing the use of GFP for PCA, Ghosh et al. (J. Am. Chem. Soc 122:5658-5659, 2000; US 2002/0146701) used a GFP PCA to study GCN4 leucine zipper oligomerization in a manner originally proposed by Michnick et al. They showed antiparallel leucine zipper-directed reassembly of GFP fragments in bacteria. A single GFP variant was chosen for these studies and a single fragmentation site was used. The authors did not disclose additional principles or methods for fragmenting a fluorescent protein based on rational design beyond the principles first described in Michnick et al. (e.g. U.S. Pat. No. 6,270,964). Moreover, other than the fragment pair used in the leucine zipper study, Ghosh and coworkers did not disclose specific assay compositions useful for PCA.

Hu et al. (Molecular Cell 9: 789-798, 2002) described a PCA based on a yellow variant of GFP, where the fragments of YFP were fused either to parallel leucine zippers or to Rel family proteins. However, additional principles and methods of engineering fluorescent proteins, and fragment compositions, were not described by Hu and coworkers. Moreover, the prior art is silent on the topic of whether mutations known to affect the properties of intact fluorescent proteins would confer similar properties on polypeptide fragments used for PCA.

Since fluorescent protein PCAs do not depend upon external cofactors or substrates for signal generation, they are particularly useful for the construction of cell-based assays. A suite of fluorescent protein PCAs would enable a large number of useful assays with differing spectral properties. For example, fluorescent proteins with high quantum yields could be engineered into PCA fragments to allow detection of rare events within cells, such as complexes between proteins expressed at very low levels, or low-affinity complexes between enzymes and their substrates. In addition, PCAs with red-shifted emissions would provide improved signal to noise relative to cellular autofluorescence which often occurs in the green channel. Importantly, fragments generating different color PCAs could be combined to allow simultaneous monitoring of two, three, or more cellular events (multicolor PCA). Finally, fluorescent protein PCAs could be used to create multicolor arrays for rapid diagnostics. For example, multicolor arrays based on antibodies binding to different antigens would allow the rapid and simultaneous detection of biowarfare agents.

OBJECTS AND ADVANTAGES OF THE INVENTION

It is an object of the present invention to provide methods for designing and engineering fluorescent protein fragments and mutant fragments for PCA.

It is a further object of the invention to describe a large number of fragment pairs and compositions useful for PCA.

Another object of the invention is to teach that any useful sequence variant of an intact fluorescent protein can be engineered into the PCA fragments, generating assays with a variety of spectral and physical properties.

A further object of the invention is to provide compositions of PCA fragments, incorporating a wide range of mutations that confer useful properties.

A still further object of the invention is to provide multicolor PCAs'.

The advantage of the invention is the ability to create 'designer' PCAs with a range of useful properties for a variety of applications.

SUMMARY OF THE INVENTION

The present invention relates to a composition comprising complementary fragments of a protein, said fragments generating an optically detectable signal when associated.

The invention also relates to fragments derived form fluorescent proteins and mutant fluorescent proteins.

The instant invention also describes complementary fragments of mutant fluorescent proteins which differ from the corresponding fragments of the wild-type protein by at least one amino acid.

The invention further relates to complementary fragments selected from the group consisting of: Seq. ID NO: 20 to Seq. ID NO: 1067.

The invention also describes a composition selected from Seq. ID NO: 20 to Seq. ID NO: 1067 which are further fused to a separate molecule.

The invention also provides a composition comprising complementary fragments of a mutant protein, said fragments generating an optically detectable signal when associated, wherein each fragment is fused to a separate molecule.

The invention is further directed to protein fragment complementation assays for the detection of molecular interactions comprising a reassembly of separate fragments from an optically detectable protein wherein reassembly of the fragments is operated by the interaction of molecular domains fused to each fragment, wherein reassembly of the fragments is independent of other molecular processes and wherein said reassembly is detected by means of reconstitution of activity of said optically detectable protein.

The invention also provides a method for detecting biomolecular interactions said method comprising: (a) selecting an appropriate optically detectable protein; (b) effecting fragmentation of said optically detectable protein such that said fragmentation results in reversible loss of protein function; (c) fusing or attaching fragments of said optically detectable protein separately to other molecules; (d) reassociating said protein fragments through interactions of the molecules that are fused or attached to said fragments; and (e) detecting the resulting optical signal.

The present invention also concerns the design and engineering of protein-fragment complementation assays based on fluorescent proteins. Methods for fragmenting fluorescent proteins and creating mutant fragments with specific properties are described, based on fluorescent proteins derived from *Aequorea*, *Anthozoa* and *Anemonia* species. Finally, a large number of fragment compositions and fragment pairs are provided that incorporate mutations with useful properties generating green, yellow, cyan, blue or red signals. Detailed examples of fluorescent protein PCAs are shown with numerous mutants of *Aequorea* fluorescent proteins, demonstrating the engineering principles and showing that mutations conferring useful properties to the full-length protein can also be conferred to the fragments. The invention also provides methods and compositions for the construction of multi-color PCAs.

BRIEF DESCRIPTION OF THE DRAWINGS

FIGS. 1*a* and 1*b* show regions in which *Aequorea* fluorescent proteins can be fragmented. FIG. 1A shows six alternative loops_(asterisked) where fragmentation can be effected relative to the linear sequence. FIG. 1B shows specific amino acid residues at the sites (see arrows), relative to the three-dimensional structure of the protein; amino acid residues at the fragmentation sites are numbered relative to wild-type GFP.

FIG. 2 depicts the strategy for design and creation of a fluorescent protein-fragment complementation assay.

FIG. 3 shows photomicrographs of PCA results in live cells, depicting the relative fluorescent intensities achieved with PCAs based on two variants of *A. victoria* (GFP PCA and YFP PCA); several different protein-protein complexes were evaluated by fluorescence microscopy 24 hours after transient transfection.

FIG. 6 shows the bright signal generated by a super-enhanced PCA (panel a) with mutations that enhance the folding of YFP fragments as compared with a non-enhanced PCA (panel b). The sub-cellular location of protein-protein complexes can also be seen by fluorescence microscopy. Individual YFP fragments are incapable of fluorescing (c and d).

DETAILED DESCRIPTION OF THE INVENTION

Fluorescent proteins are particularly attractive for PCAs because they require no external substrates or probes for the generation of the fluorescent signal. However, fluorescent proteins present certain design challenges because of their unique structure and the requirement for internal formation of an active chromophore for generation of the fluorescent signal. The present invention encompasses the design criteria for fragmentation of a fluorescent protein, which are described below.

FIG. 2 describes the steps involved in creating a PCA based on a fluorescent protein. The first step is the selection of a fluorescent protein and its corresponding DNA sequence. Any fluorescent protein can be used for PCA based on the design principles that are the subject of the present invention. The choice of a fluorescent protein depends on the desired wavelength, instrumentation, and sensitivity required for the assay of interest. DNA fragments of the selected reporter are then made, using one of the methods described herein. In the first example, we describe the use of rational design to determine where to fragment a fluorescent protein. Because the fluorescent proteins have similar structures, we first describe the design principles for the example of *A. victoria* GFP.

Figure 1B:
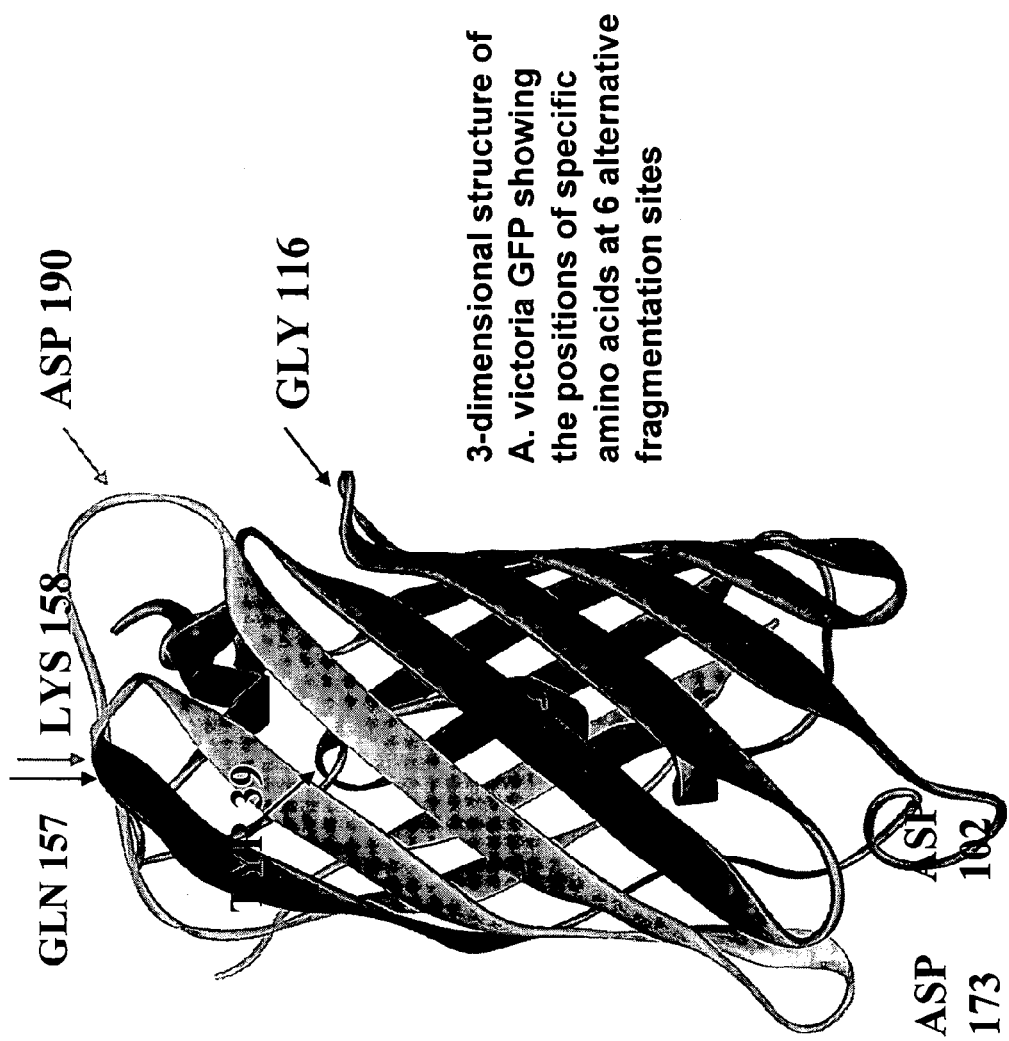

GFP is an 11-stranded β-barrel with the highly unusual feature of having an α-helix that is thread through the central axis of the β-barrel (Ormo et al., Science 273:1392-95, 1996; F. Yang et al., *Nat. Biotechnol.* 14:1246-5121, 1996; R. Heim et al., Nature 373: 663-64, 1995). FIG. 1A shows a two-dimensional view of the protein; the 11 strands of the barrel are shown in relation to the central alpha-helix, and the amino acid positions at the ends of the barrel are numbered. FIG. 1B shows the 3-dimensional structure of the folded protein; the positions of specific residues at the loops are noted (all numbering is relative to the wild-type GFP). The chromophore is attached to the α-helix and is buried almost completely in the center of the β-barrel cylinder. Almost all the primary sequence is used to build the β-barrel and axial helix. The chromophore is a p-hydroxybenzylidene-imidazolinone formed from residues 65-67, which are Ser(Thr)-Tyr-Gly in the native protein (1,2). The chromophore is a 4-(p-hydroxy-benzylidene)imidazolidin-5-one attached to the peptide backbone through the 1- and 2-positions of the ring. First, GFP folds into a nearly native conformation, then the imidazolinone is formed by nucleophilic attack of the amide of Gly67 on the carbonyl of residue 65, followed by dehydration. Finally, molecular oxygen dehydrogenates the Cα-Cβ bond of residue 66 to put its aromatic group into conjugation with the imidazolinone (3).

There are obvious features of the structure that should not be disrupted and therefore, by default, alternatives to such regions are chosen for fragmentation. The design criteria for fluorescent protein PCAs include the following:

(1) Fragmentation is made in β-turns or loops at the extreme ends of individual strands so as not to disrupt the barrel structure. Preferred regions for fragmentation are shown in FIG. 1A, with specific amino acids corresponding to the regions shown in the 3-dimensional structure in FIG. 1B.

(2) The chromophore is deeply buried in the β-barrel. It is likely that this is required to isolate the chromophore coding sequence, both to assure efficient formation of the chromophore and to maintain both rigid conformation and coordination to the side chains of other amino acids that provide GFP with its unique spectral characteristics. Isolation of the chromophore from solvent is maintained both by being embedded in the β-barrel and also by barrel "capping" structures at either end of the barrel. These caps include: (a) Cap at N-terminus of internal helix: Residues 19-30 strand; Residues 133-143 hairpin; Residues 50-57 (This is the N-terminus of the internal helix); and (b) Cap at C-terminus of internal helix: Residues 1-10, helix; Residues 77-98, helix; Residues 191-197, strand. Neither of these regions should be disrupted.

Figure 4:
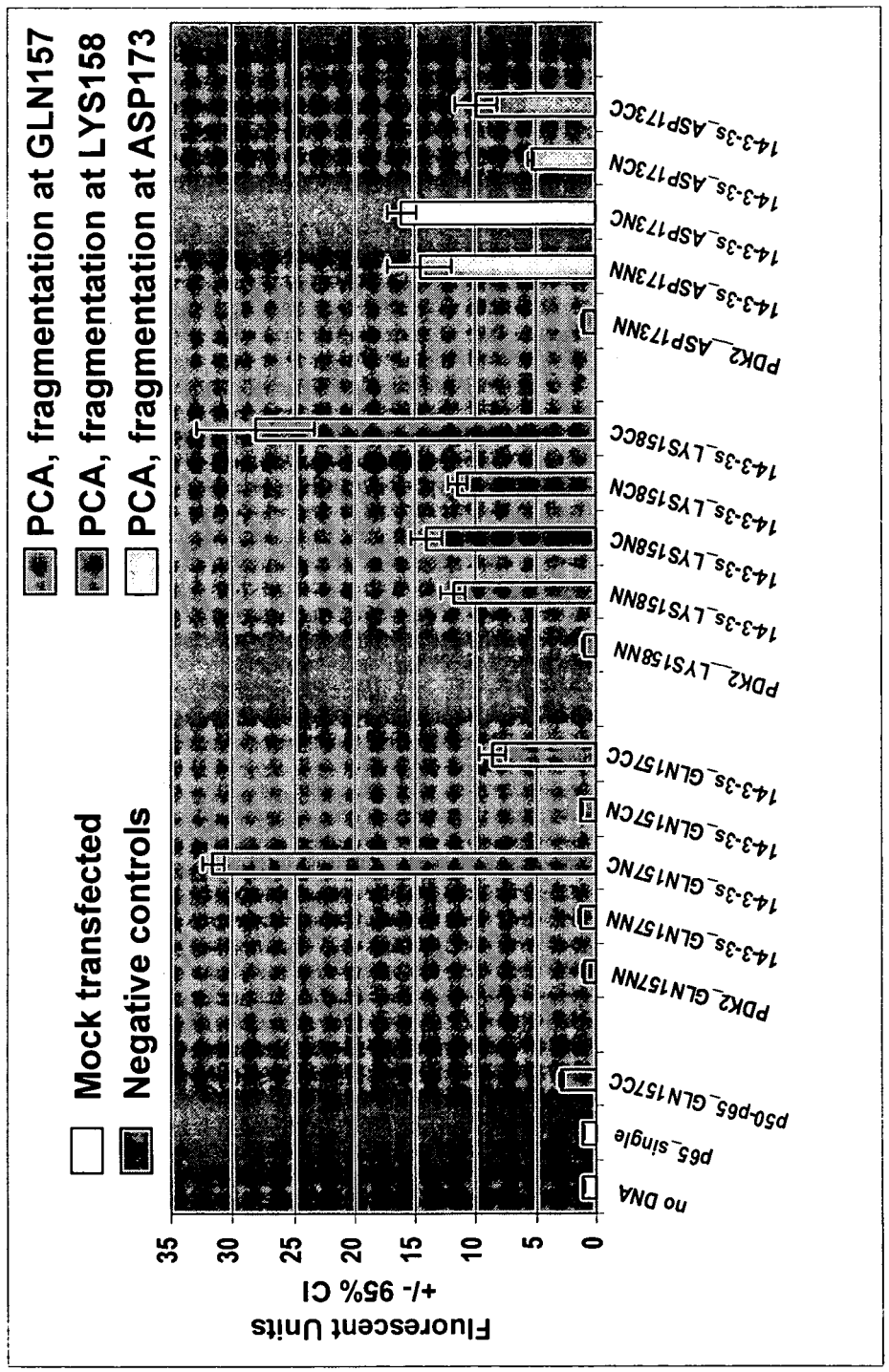
FIG. 4 shows PCAs based on fragment pairs generated from several alternative fragmentation sites as depicted in FIG. 1*a* and 1*b*.

Based on these criteria the optimal fragmentation regions are shown in FIG. 1*a* relative to the linear model of the GFP structure. Fragmentation can be effected in one of the loops comprising amino acid residues 38-40 (region 1); amino acids 101-103 (region 2); amino acids 114-118 (region 3); amino acids 154-160 (region 4); amino acids 171-175 (region 5); or amino acids 188-190 (region 6). Fragmentation can be effected at one of the amino acids within those regions. It will be obvious to one skilled in the art that the exact residue at which the fragmentation is effected may vary within the designated loops without having a significant impact on the ability of the fragments to fold and reconstitute an active structure, as long as the design criteria described above and in U.S. Pat. No. 6,270,964 are followed. To prove the design principle, we present examples (FIG. 4) of successful PCA construction based on fragmentation of YFP at three different amino acids selected from the regions listed above.

While fragmentation of proteins for PCA is generally based on rational dissection of the polypeptide chain as described in the present invention, a number of other engineering approaches can be used that will be well known to one skilled in the art. For example, we have previously proposed an alternative approach based on the use of 5' exonucleases to generate libraries of fragments to search for optimal pairs (Michnick, et al. U.S. Pat. No. 6,270,964).

Figure 9:
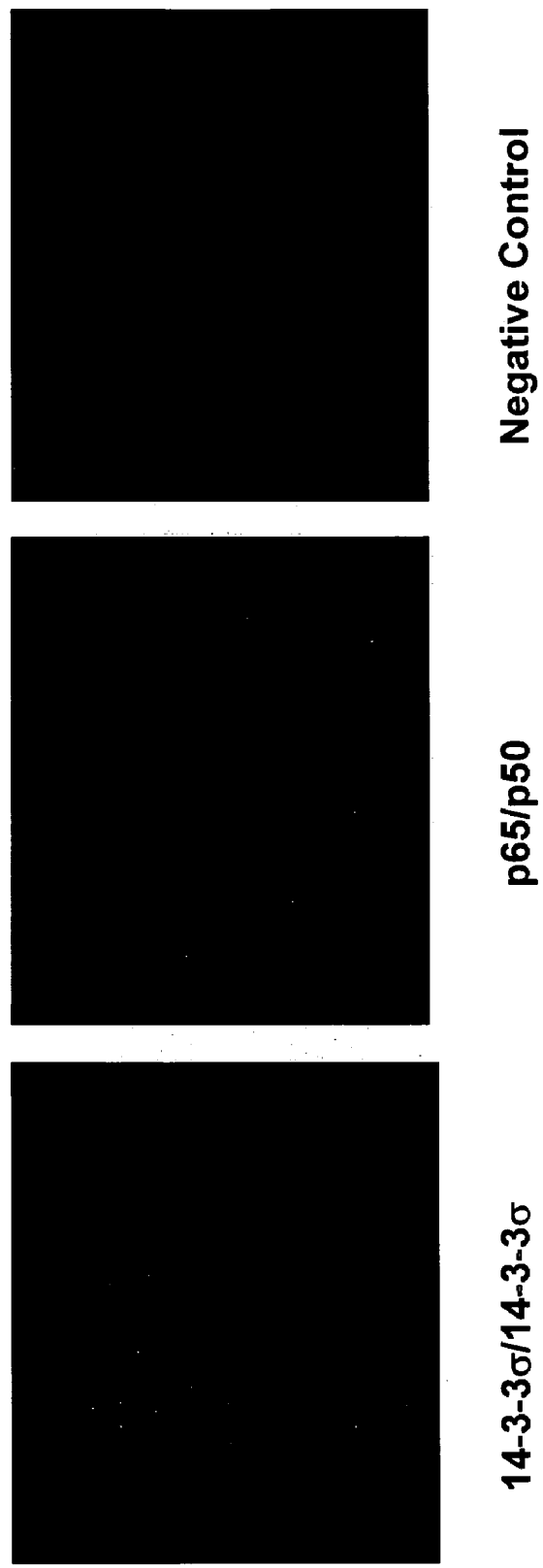
FIG. 9 demonstrates a spectrally shifted PCA based on mutant fluorescent protein fragments generating a blue signal in the presence of a protein-protein interaction FIG. 10 demonstrates multi-color PCA, wherein a single fusion protein (p65 in this example) tagged with a fragment corresponding to the C-terminus of a fluorescent protein is capable of generating two different fluorescent PCAs in the same cell depending upon the amino acid sequence of the reporter fragment fused to the proteins that interact with the first protein. Multi-color PCAs allow for the detection and quantification of different protein-protein complexes within the same cells.

In the present invention we generated fragments of the full-length cDNA for GFP using PCR to amplify fragments of interest. Alternatively, oligonucleotides encoding fragments can simply be synthesized using standard oligonucleotide synthesis techniques; this approach was taken to generate a PCA based on a cyan fluorescent protein (FIG. 9). In a preferred embodiment, mutant fragments of a fluorescent protein are used, having properties tailored to the biological application and the instrumentation to be used. To generate mutant fragments, as described below in detail, we utilized site-directed mutagenesis of GFP in order to obtain fragments that when reconstituted would have altered fluorescence properties or superior folding or maturation rates and stabilities. Site-directed mutagenesis is achieved by any of a number of approaches that are well known to one skilled in the art (see M M Ling & B H Robinson, 1997, Approaches to DNA mutagenesis: an overview. Anal Biochem 254:157-78). Selected examples of such methods are provided here; however, these examples are not intended to be limiting for the practice of this invention. Suitable methods could include combinations of random mutagenesis and directed evolution or DNA shuffling schemes (A. L. Kurtzman et al., 2001, Advances in directed protein evolution by recursive genetic recombination: applications to therapeutic proteins, Curr Opin Biotechnol 2001 August; 12(4):361-70; SW Santoro et al., 2002, Directed evolution of the site specificity of Cre recombinase. Proc Natl Acad Sci USA 2002 99:4185-90; Z. Shao et al., 1996, Engineering new functions and altering existing functions, Curr Opin Struct Biol 6:513-8; S. Harayama, 1998, Artificial evolution by DNA shuffling, Trends Biotechnol 1998, 16:76-82); assembly PCR or gene synthesis approaches (WP Stemmer et al., 1995, Single-step assembly of a gene and entire plasmid from large numbers of oligodeoxyribonucleotides, Gene 164(1):49-53; R M Horton et al. 1993, Gene splicing by overlap extension. Methods Enzymol. 217:270-9), or fragmentation by exo- or endo-nuclease digestion (M. Kitabatake and H. Inokuchi, 1993, A simplified method for generating step-wise deletions using PCR, Gene 123:59-61; S. Henikoff, 1990, Ordered deletions for DNA sequencing and in vitro mutagenesis by polymerase extension and exonuclease III gapping of circular templates, Nucleic Acids Res 18(10):2961-6). A particularly powerful method is based on 5'-template-assisted long-range plasmid polymerization as exemplified by a number of commercial mutagenesis kits, for example the QuickChange™ system (Stratagene). In addition, various forms of directed evolution based on DNA shuffling could also be used to generate completely novel PCAs.

Once the DNA fragments F1 and F2 of the gene encoding the fluorescent protein are generated, each fragment is individually fused in frame with a gene encoding a protein or polypeptide of interest in a suitable expression vector. A variety of standard or novel expression vectors can be chosen based on the cell type and desired expression level; such vectors and their characteristics will be well known to one skilled in the art. Optimally, a flexible linker, such as that described in Example 1 below, is fused between the fluorescent protein fragment and the gene of interest to facilitate fragment complementation. Therefore, each expression vector codes for a fusion protein, consisting of an operably linked gene of interest, a flexible linker, and either F1 or F2 of the chosen fluorescent protein. As shown in FIG. 2, since either F1 or F2 can be fused to the gene of interest and the orientation of the fusion can be either 5' or 3' relative to the gene of interest, four different DNA constructs are possible for any single gene of interest. (It should be noted that if the fluorescent protein fragment is at the 5' end of the construct, it will be preceded by an initiating methionine (atg codon), whereas if the fragment is at the 3' end of the construct, the gene of interest will be preceded by the initiating methionine (atg codon)). Therefore, the invention covers not only F1 fragments that have a naturally occurring initiating methionine, but also the same F1 fragments that have been modified to remove the initiating methionine when the F1 fragment is to be at the 3' end of the construct. Similarly, the invention covers F2 fragments that naturally do not begin with an initiating methionine, but also those same F2 fragments that have been modified include an initiating methionine when the F2 fragment is to be at the 5' end of the construct.

To generate the PCA for a pair of proteins A and B, constructs encoding A and B fused separately to complementary fluorescent protein fragments F1 and F2 are co-transfected into cells. If proteins A and B interact, fragments F1 and F2 are brought into close proximity where they are capable of folding and reconstituting an active chromophore. The fluorescent signal can then be measured by a variety of standard methods, including fluorescence spectroscopy, flow cytometry (FACS), or microscopy. All of these methods can be used in automated, high-throughput formats using instrumentation well known to those skilled in the art. As described below, novel multicolor fluorescent PCAs can also be generated by using more than two construct pairs simultaneously. Finally, although it is expedient to carry out the engineering and construction of PCAs at the DNA level and then either allow a cell to produce the fusion proteins, it is not essential. For example, fusion proteins can be made in vitro using in vitro expression techniques that are well known to those skilled in the art. In addition, for in vitro PCAs, fusion polypeptides could be produced synthetically by peptide synthesis, or by ligation of peptide fragments encoding molecules of interest to create peptide fusions with the fluorescent protein fragments.

The structural homology amongst fluorescent proteins from various marine organisms enables the same design criteria described for GFP to be applied to other fluorescent proteins such as those recently described from Discosoma and from Anemonia. Therefore, in addition to GFP variants we present additional PCAs based on fragments of the mono-merized Red Fluorescent Protein (mRFP1, derived from DsRed); and a fluorescent protein KFP1 that can be transiently activated (kindled) by irradiation of the chromophore at specific wavelengths based on the fluorescent protein 'asCP' from *Anemonia sulcata*. (Chudakov, D. M., Belousov, et al. 2003, Nat Biotechnol 21, 191-194). In both cases the fluorescent proteins are homologues of GFP at the amino acid level.

The red-shifted fluorescent PCAs that are the subject of this invention will be particularly useful for biological applications in which there is significant auto-fluorescence in the green channel. For example, red-shifted PCAs will be particularly useful for cDNA library screening applications using flow sorting. in this case the positive cell population expressing a protein-protein complex detected by an RFP PCA will be shifted away from the background population, readily allowing flow sorting of the positive cells.

DsRed from Discosoma has been demonstrated to be a structural homologue of GFP. DsRed is a 28-kDa polypeptide that has essentially the same chromophore as GFP, which is auto-catalytically formed from an internal Gln-Tyr-Gly (residues 66-68) tripeptide. DsRed is remarkably similar structurally to *A. victoria* GFP. In fact, the overall fold of DsRed is virtually identical to GFP, consisting of a slightly irregular 11-stranded beta-barrel (described as a beta can) with a coaxial central helix and alpha-helical caps on the barrel ends. The novel fragments that are the subject of this invention are based directly on examining of the RFP structure (Wall, M. A., et al., The structural basis for red fluorescence in the tetrameric GFP homolog DsRed, Nat Struct Biol 7, 1133-1138 (2000)) and using the rational design criteria described above for fragmentation of GFP. The amino acid sequence of mRFP1 is shown in Table 5 aligned with the sequence of *A. Victoria* GFP, showing alignment of the alternative fragmentation sites. The present invention encompasses nucleic acid sequences and polypeptide fragments generated by fragmentation of mRFP1 at the following alternative fragmentation sites: amino acids 38-40 (region 1); amino acids 100-102 (region 2); amino acids 113-117 (region 3); amino acids 152-156 (region 4); amino acids 167-171 (region 5); amino acids 182-184 (region 6). The positions of specific amino acid residues are shown for Glutamate 39 (E39), Aspartate 101 (D101), Aspartate 115 (D115), Glutamate 153 (E153), Aspartate 169 (D169), or Lysine 184 (K184). The fragmentation sites relative to the nucleic acid sequence encoding the full-length mRFP1 polypeptide are depicted in Table 6.

TABLE 4

Multiple alignment of coral (*Anthozoa* sp.) fluorescent proteins. The numbering is based on *A. victoria* GFP (M.V. Matz et al., Nature Biotech. 17: 969-973, 1999). Two proteins from *Zoanthus* and two from *Discosoma* are compared pairwise. Introduced gaps are represented by dots. In the consensus sequences ("cns"), "0" marks an aromatic residue (Phe, Tyr, Trp, His); "@" = bulky hydrophobic residues (Val, Leu, Ile, Met, Phe, Trp); "+" = positively charged residues (His, Arg, Lys); "−" = negatively charged residues (Asp, Glu). "FP', fluorescent protein; 'z', *Zoanthus*; 'ds', *Discosoma*; 'dr', *Discosoma* 'red'; 'c', *Clavularia*; 'cns', consensus. DrFP583 is commonly referred to as 'DsRed' where 583 refers to the emission maximum at 583 nm (at an excitation maximum of 558 nm). By homology to the fragmentation sites chosen for GFP (FIG. 1A and 1B), alternative fragmentation sites of the coral fluorescent proteins which are the subject of the current invention are underlined.

```
              10         20         30         40         50
MSKGEELFTG.VVPILVELDGDVNGHKFSVSGEGEGDATYGKLTLKFICTT.GKLPVP...W    GFP      (SEQ ID NO: 2)

MAQSKHGLTK.FMTMKYRMEGCVDGHKFVITGEGIGYPFKGKQAINLCVV..EGGPLPFAE    zFP506   (SEQ ID NO: 9)
MAHSKHGLKE.EMTMKYHMEGCVNGHKFVITGEGIGYPFKGKQTINLCVI..EGGPLPFSE    zFP538   (SEQ ID NO: 10)

MSCSKSVIKE.EMLIDLHLEGTFNGHYFFIKGKGKGQPNEGTNTVTLEVT  KGGPLPFGW    dsFP483  (SEQ ID NO: 11)
MRSSKNVIKE.FMRFKVRMEGTVNGHEFFIEGEGEGRPYEGHNTVKLKVT..KGGPLPFAW    drFP583  (SEQ ID NO: 12)

MALSNKFIGD.DMKMTYHMDGCVNGHYFTVKGEGNGKPYEGTQTSTFKVTMANGGPLAFSF    amFP486  (SEQ ID NO: 13)
KALTTMGVIKPDMKIKLKMEGNVNGHAFVIEGEGEGKPYDGTHTLNLEVKMAEGAPLPFSY    cFP484   (SEQ ID NO: 14)
MSKGEELFTG.VVPILVELDGDVNGHKFSVSGEGEGDATYGKLTLKFICTT.GKLPVP...W    GFP

MAQSKHGLTK.FMTMKYRMEGCVDGHKFVITGEGIGYPFKGKQAINLCVV..EGGPLPFAE    zFP506
MAHSKHGLKE.EMTMKYHMEGCVNGHKFVITGEGIGYPFKGKQTINLCVI..EGGPLPFSE    zFP538

MSCSKSVIKE.EMLIDLHLEGTFNGHYFFIKGKGKGQPNEGTNTVTLEVT  KGGPLPFGW    dsFP483
MRSSKNVIKE.FMRFKVRMEGTVNGHEFFIEGEGEGRPYEGHNTVKLKVT..KGGPLPFAW    drFP583

MALSNKFIGD.DMKMTYHMDGCVNGHYFTVKGEGNGKPYEGTQTSTFKVTMANGGPLAFSF    amFP486
KALTTMGVIKPDMKIKLKMEGNVNGHAFVIEGEGEGKPYDGTHTLNLEVKMAEGAPLPFSY    cFP484 s          M  @      EG vnGH  F  @ GeG  G  Po G   t@ @ V       GgPLpF     cns. Anthozoa
               @  @      EG vnGH  F  @ GeG  G     G   t@ @         P@p        cns. all 60         70         80         90        100        110
PTLVTTFSYGVQCFSRYPDHMKQHDFFKSAMPEGYVQERTIFFKDDGNYKTRAEVKFEGD..    GFP DILSAAFNYGNRVFTEYPQDIV..DYFKNSCPAGYTWDRSFLFEDGAVCICNADITVSVEEN   zFP506
DILSAGFKYGDRIFTEYPQDIV..DYFKNSCPAGYTWGRSFLFEDGAVCICNVDITVSVKEN   zFP538

HILCPQFQYGNKAFVHHPDNIH..DYLKLSFPEGYTWERSMHFEDGGLCCITNDISLTGN..   dsFP483
DILSPQFQYGSKVYVKHPADIP..DYKKLSFPEGFKWERVMNFEDGGVVTVTQDSSLQDG..   dsFP583

DILSTVFKYGNRCFTAYPTSMP..DYFKQAFPDGMSYERTFTYEDGGVATASWEISLKGN..   amFP486
DILSNAFQYGNRALTKYPDDIA..DYFKQSFPEGYSWERTMTFEDKGIVKVKSDISMEED..   cFP484 dILs    F  YGn+  f   yP  @     DYfK  sfPeGo  wER  @ OEDgg@    Dis@        cns. Anthozoa
     iL     F  YG    f   yP  @     DyfK    PeGo   ER  @ O D  g    D@ @        cns. all
```

TABLE 4-continued

Multiple alignment of coral (*Anthozoa* sp.) fluorescent proteins. The numbering is based on *A. victoria* GFP (M.V. Matz et al., Nature Biotech. 17: 969-973, 1999). Two proteins from *Zoanthus* and two from *Discosoma* are compared pairwise. Introduced gaps are represented by dots. In the consensus sequences ("cns"), "0" marks an aromatic residue (Phe, Tyr, Trp, His); "@" = bulky hydrophobic residues (Val, Leu, Ile, Met, Phe, Trp); "+" = positively charged residues (His, Arg, Lys); "-" = negatively charged residues (Asp, Glu). "FP", fluorescent protein; 'z', *Zoanthus*; 'ds', *Discosoma*; 'dr', *Discosoma* 'red'; 'c', *Clavularia*; 'cns', consensus. DrFP583 is commonly referred to as 'DsRed' where 583 refers to the emission maximum at 583 nm (at an excitation maximum of 558 nm). By homology to the fragmentation sites chosen for GFP (FIG. 1A and 1B), alternative fragmentation sites of the coral fluorescent proteins which are the subject of the current invention are underlined.

```
          120       130       140       150       160       170
TLVNRIELKGIDFKEDGNILGHKLEYNYNSHNVYIMADKQKNGIKVNFKIRHNIEDGSVQL    GFP

CMYHESKFYGVNFPADGPVM.KKMTDNWEPSCEKIIPVPKQGILKGDVSMYLLLKDGGRLR    zFP506
CIYHKSIFNGMNFPADGPVM.KKMTTNWEASCEKIMPVPKQGILKGDVSMYLLLKDGGRYR    zFP538

CFYYDIKFTGLNFPPNGPVV.QKKTTGWEPSTERLYP..RDGVLIGDIHHALTVEGGGHYA    dsFP483
CFIYKVKFIGVNFPSDGPVM.QKKTMGWEASTERLYP..RDGVLKGEIHKALKLKDGGHYL    drFP583

CFEHKSTFHGVNFPADGPVM.AKKTTGWDPSFEKMTV..CDGILKGDVTAFLMLQGGGNYR    amFP486
SFIYEIRFDGMNFPPNGPVM.QKKTLKWEPSTEIMYV..RDGVLVGDISHSLLLEGGGHYR    cFP484
c@ O    f G@NFP dGPVm  KkT  Weps E+@    dG@L+GD@    L  l  GG+y   cns. Anthozoa
 @      @ G@nF  dG @@   K     o    @        @+   @       @  G   cns. all 180       190       200       210       220       230
ADHYQQNTPIGDG.PVLLPDNHYLSTQSALSKDPNEKRDHMVLLEFVTAAGITHGMDELYK    GFP CQFDTVYKAKSV..PRKMPDWHFIQHKLTREDRSDAKNQKWHLTEHAIASGSALP         zFP506
CQFDTVYKAKSV..PSKMPEWHFIQHKLLREDRSDAKNQKWQLTEHAIAFPSALA         zFP538

CDIKTVYRAKKA..ALKMPGYHYVDTKLVIWNNDKEFM.KVEEHEIAVARHHPFYEPKKDK   dsFP483
VEFKSIYMAKKA..PVQLPGYYYVDSKLDITSHNEDYT.IVEQYERTEGRHHLFL         drFP583

CQFHTSYKTKK...PVTMPPNHVVEHRIARTDLDKGGN.SVQLTEHAVAHITSVVPF       amFP486
CDFKSIYAKK...VVKLPDYHFVDHRIEILNHDKDYN.KVTLYENAVARYSLLPSQA       cFP484 c @ t@YkaKk   pvk@P   ho@Dh+@          @ l E a@a                cns. Anthozoa
              p  @P   ho@               @ l E  a                cns. all
```

TABLE 5

Amino acid alignment of mRFP1 (SEQ ID NO: 16) with *A. victoria* GFP (SEQ ID NO: 2) showing alternative fragmentation sites (underlined) that are the subject of the present invention

```
# Aligned_sequences: 2
# 1: A. victoria GFP
# 2: mRFP1
# Matrix: EBLOSUM62
# Gap_penalty: 12
# Extend_penalty: 2

# Length: 240
# Identity:    58/240 (24.2%)
# Similarity: 109/240 (45.4%)
# Gaps:        17/240 (7.1%)
# Score: 186

10        20        30        40        50
GFP      MSKGEELFTGVVPILVELDGDVNGHKFSVSGEGEGDATYGKLTLKFICTT
         :...:...  ..  :....:::::..:..:...:::::  :   : :.  :
mRFP1    MASSEDVIKEFMRFKVRMEGSVNGHEFEIEGEGEGRPYEGTQTAKLKVTK
                     10        20        30        40        50

60        70        80        90
GFP      G-KLPVPWPTLVTTFSYGVQCFSRYPDHMKRHDFFKSAMPEGYVQERTIF
         : ::   : :   :  ... ...  :::::  :  .::::.  .
mRFP1    GGPLPFAWDILSPQFQYGSKAYVKHPADIP--DYLKLSFPEGFKWERVMN
                     60        70        80        90

100       110       120       130       140
```

TABLE 5-continued

Amino acid alignment of mRFP1 (SEQ ID NO: 16) with
A. victoria GFP (SEQ ID NO: 2) showing alternative
fragmentation sites (underlined) that are the
subject of the present invention

```
GFP     FKDDGNYKTRAEVKFEGDTLVNRIELKGIDFKEDGNILGHK-LEYNYNSH
        :.: :    .   .  ...   .. ...:.:  .: .:: ..  : .. ...
mRFP1   FEDGGVVTVTQDSSLQDGEFIYKVKLRGTNFPSDGPVMQKKTMGWEASTE
        100       110       120       130       140

150       160       170       180       190
GFP     NVYIMADKQKNGIKVNFKIRHNIEDGSVQLADHYQQNTPIGDGPVLLPDN
         ..:    .  ...:..:  ...:.  :.       ::   ::  ::
mRFP1   RMY-----PEDGALKGEIKMRLKLKDGGHYDAE--VKTTYMAKKPVQLPGA
           150       160       170       180       190

200       210       220       230
GFP     HYLSTQSALSKDPNEKRDHMVLLEFVTAAGITHGMDELYK
         .   .   ..   ....:. .. ..  :     .:   .
mRFP1   YKTDIKLDIT---SHNEDYTIVEQYERA----EGRHSTGA
             200       210       220
```

TABLE 6 mRFP1 full length nucleic acid (SEQ ID NO: 15) and amino acid sequence
(SEQ ID NO: 16). Alternative fragmentation sites that are the subject of
the present invention are shown (underlined) at the following regions:
amino acids 38-40 (region 1); amino acids 100-102 (region 2); amino acids
152-156 (region 3); amino acids 167-171 (region 4); amino acids 182-191
(region 5). The positions of specific amino acid residues at the
fragmentation sites for mRFP1 are shown for Glutamate 39 (E39), Aspartate
101 (D101), Aspartate 115 (D115), Glutamate 153 (E153), Aspartate 169
(D169), or Lysine 184 (K184)

```
atg gcc tcc tcc gag gac gtc atc aag gag ttc atg cgc ttc aag gtg cgc atg gag ggc
 M   A   S   S   E   D   V   I   K   E   F   M   R   F   K   V   R   M   E   G
 1           5               10              15              20 tcc gtg aac ggc cac gag ttc gag atc gag ggc gag ggc gag ggc cgc ccc tac gag ggc
 S   V   N   G   H   E   F   E   I   E   G   E   G   E   G   R   P   Y   E   G
21              25              30              35             E39  40 acc cag acc gcc aag ctg aag gtg acc aag ggc ggc ccc ctg ccc ttc gcc tgg gac atc
 T   Q   T   A   K   L   K   V   T   K   G   G   P   L   P   F   A   W   D   I
41              45              50              55              60 ctg tcc cct cag ttc cag tac ggc tcc aag gcc tac gtg aag cac ccc gcc gac atc ccc
 L   S   P   Q   F   Q   Y   G   S   K   A   Y   V   K   H   P   A   D   I   P
61              65              70              75              80 gac tac ttg aag ctg tcc ttc ccc gag ggc ttc aag tgg gag cgc gtg atg aac ttc gag
 D   Y   L   K   L   S   F   P   E   G   F   K   W   E   R   V   M   N   F   E
81              85              90              95             100 gac ggc ggc gtg gtg acc gtg acc cag gac tcc tcc ctg cag gac ggc gag ttc atc tac
 D   G   G   V   V   T   V   T   Q   D   S   S   L   Q   D   G   E   F   I   Y
D101           105             110            D115             120 aag gtg aag ctg cgc ggc acc aac ttc ccc tcc gac ggc ccc gta atg cag aag aag acc
 K   V   K   L   R   G   T   N   F   P   S   D   G   P   V   M   Q   K   K   T
121             125             130             135             140 atg ggc tgg gag gcc tcc acc gag cgg atg tac ccc gag gac ggc gcc ctg aag ggc gag
 M   G   W   E   A   S   T   E   R   M   Y   P   E   D   G   A   L   K   G   E
141             145             150            E153  155             160 atc aag atg agg ctg aag ctg aag gac ggc cac tac gac gcc gag gtc aag acc acc
 I   K   M   R   L   K   L   K   D   G   H   Y   D   A   E   V   K   T   T
161             165            D169  170             175             180 tac atg gcc aag aag ccc gtg cag ctg ccc ggc gcc tac aag acc gac atc aag ctg gac
 Y   M   A   K   K   P   V   Q   L   P   G   A   Y   K   T   D   I   K   L   D
181            K184  185             190             195             200
```

TABLE 6-continued mRFP1 full length nucleic acid (SEQ ID NO: 15) and amino acid sequence (SEQ ID NO: 16). Alternative fragmentation sites that are the subject of the present invention are shown at the following regions (underlined): amino acids 38-40 (region 1); amino acids 100-102 (region 2); amino acids 152-156 (region 3); amino acids 167-171 (region 4); amino acids 182-191 (region 5). The positions of specific amino acid residues at the fragmentation sites for mRFP1 are shown for Glutamate 39 (E39), Aspartate 101 (D101), Aspartate 115 (D115), Glutamate 153 (E153), Aspartate 169 (D169), or Lysine 184 (K184)

```
atc acc tcc cac aac gag gac tac acc atc gtg gaa cag tac gag cgc gcc gag ggc cgc
 I   T   S   H   N   E   D   Y   T   I   V   E   Q   Y   E   R   A   E   G   R
201             205                 210                 215                 220 cac tcc acc ggc gcc
 H   S   T   G   A
221             225
```

A PCA based on kindling fluorescent protein (KFP1) is also the subject of the present invention. In the case of KFP 1, which is a variant of the fluorescent protein derived from *Anemonia sulcata*, the alternative fragmentation sites are based on the alignment of KFP 1 to GFP as shown in Table 7. Table 8 shows the fragmentation sites relative to the full-length nucleotide and amino acid sequence of KFP 1.

TABLE 7

Amino acid alignment of kindling fluorescent protein (KFP1) (SEQ ID NO: 18) with *A. Victoria* GFP (SEQ ID NO: 2), showing alternative fragmentation sites (underlined) that are the subject of the present invention

```

# Aligned_sequences: 2
# 1: A. Victoria GFP
# 2: kindling fluorescent protein (KFP1)
# Matrix: EBLOSUM62
# Gap_penalty: 12
# Extend_penalty: 2

# Length: 241
# Identity:    57/241 (23.7%)
# Similarity:  98/241 (40.7%)
# Gaps:        12/241 (5.0%)
# Score: 145

10        20        30        40
GFP       MSKGEELFTGVVPILVELDGDVNGHKFSVSGEGEGDATYGKLTLKF-ICT
          :...     :.:  ..:. ...: ::::  :.  :.::::.   :    .:..  .
KFP1      MAS---LLTETMPFKTTIEGTVNGHCFKCIGKGEGNEFEGTQEMKIEVIE
                   10        20        30        40

50        60        70        80        90
GFP       TGKLPVPWPTLVTTFSYGVQCFSRYPDHMKRHDFFKSAMPEGYVQERTIF
          :  ::     .  :  :.      ::  .  .:. .         :.::. .. ::: ...    :::
KFP1      GGPLPFAFHILSTSCMYGSKTFIKYVSGIP--DYFKQSFPEGFTWERTTT
                   50        60        70        80        90

100       110       120       130       140
GFP       FKDDGNYKTRAEVKFEGDTLVNRIELKGIDFKEDGNILGHKLEYNYNSHN
          ..:  :        ..  ......::  ::    ....  :  .:  ::  ....:.       . .
KFP1      YEDGGFLTAHQDTSLDGDCLVYKVKILGNNFPADGPVMQNKVGRWEPGTE
                   100       110       120       130       140

150       160       170       180       190
GFP       VYIMADKQKNGIKVNFKIRHNIEDGSVQLADHYQQNTPIG--DGPVLLPD
          .    .:   .:  ..           .    . .:       :...  :         :  ..
KFP1      IVYEVDGVLRGQSLMALKCPGGRHLTCHLHTTYRSKKPASALKMPGFHFE
                   150       160       170       180       190

200       210       220       230
GFP       NHYLSTQSALSKDPNEKRDHMVLLEFVTAAGITHGMDELYK
             .:   ..  ..:    ::   ..  ::      :       ..
KFP1      DHRIEIMEEVEKGKCYKQYEAAVGRYCDAAPSKLG---HN
                   200       210       220       230
```

TABLE 8

Kindling fluorescent protein (KFP1) full length nucleic acid
(SEQ ID NO: 17) and amino acid sequence (SEQ ID NO: 18). Alternative
fragmentation sites that are the subject of the present invention
are shown at the underlined regions: residues 35-37 (region 1);
residues 97-99 (region 2); residues 110-114 (region 3); residues
150-156 (region 4); residues 167-171 (region 5); residues 184-195
(region 6). The positions of specific amino acid residues at the
fragmentation sites for KFP1 are shown for Glutamate 36 (E36),
Aspartate 98 (D98), Glycine 112 (G112), Valine 153 (V153),
Histidine 169 (H169), or Alanine 186 (A186)

```
atg gcc tcc ctg ctg acc gag acc atg ccc ttc aag acc acc atc gag ggc acc gtg aac
 M   A   S   L   L   T   E   T   M   P   F   K   T   T   I   E   G   T   V   N
 1               5                  10                  15                  20 ggc cac tgc ttc aag tgc atc ggc aag ggc gag ggc aac ccc ttc gag ggc acc cag gag
 G   H   C   F   K   C   I   G   K   G   E   G   N   P   F   E   G   T   Q   E
                 25                  30                  35 E36                 40 atg aag atc gag gtg atc gag ggc ggc ccc ctg ccc ttc gcc ttc cac atc ctg tcc acc
 M   K   I   E   V   I   E   G   G   P   L   P   F   A   F   H   I   L   S   T
                 45                  50                  55                  60 tcc tgc atg tac ggc tcc aag acc ttc atc aag tac gtg tcc ggc atc ccc gac tac ttc
 S   C   M   Y   G   S   K   T   F   I   K   Y   V   S   G   I   P   D   Y   F
                 65                  70                  75                  80 aag cag tcc ttc ccc gag ggc ttc acc tgg gag cgc acc acc tac gag gac ggc ggc
 K   Q   S   F   P   E   G   F   T   W   E   R   T   T   T   Y   E   D   G   G
                 85                  90                  95     D98            100 ttc ctg acc gcc cac cag gac acc tcc ctg gac ggc gac tgc ctg gtg tac aag gtg aag
 F   L   T   A   H   Q   D   T   S   L   D   G   D   C   L   V   Y   K   V   K
                105                 110     G112        115                 120 atc ctg ggt aac aac ttc ccc gcc gac ggc ccc gtg atg cag aac aag gtc ggc cgc tgg
 I   L   G   N   N   F   P   A   D   G   P   V   M   Q   N   K   V   G   R   W
                125                 130                 135                 140 gag ccc gga acc gag atc gtg tac gag gtg gac ggc gtg ctg cgc ggc cag tcc ctg atg
 E   P   G   T   E   I   V   Y   E   V   D   G   V   L   R   G   Q   S   L   M
                145                 150     V153        155                 160 gcc ctg aag tgc ccc ggc ggc cgg cac ctg acc tgc cac ctg cac acc acc tac cgc tcc
 A   L   K   C   P   G   G   R   H   L   T   C   H   L   H   T   T   Y   R   S
                165             H169 170                 175                 180 aag aag ccc gcc tcc gcc ctg aag atg ccc ggc ttc cac ttc gag gac cac cgc atc gag
 K   K   P   A   S   A   L   K   M   P   G   F   H   F   E   D   H   R   I   E
                185 A186            190                 195                 200 atc atg gag gag gtg gag aag ggc aag tgc tac aag cag tac gag gcc gcc gtg ggc cgc
 I   M   E   E   V   E   K   G   K   C   Y   K   Q   Y   E   A   A   V   G   R
                205                 210                 215                 220 tac tgc gac gcc gcc ccc tcc aag ctg ggc cac aac
 Y   C   D   A   A   P   S   K   L   G   H   N
                225                 230
```

It is a feature of PCA that the reassembled fragments are capable of re-creating the activity of the intact reporter from which the fragments are derived. For example, for a PCA based on dihydrofolate reductase (DHFR), the reassembled fragments are capable of binding methotrexate in a manner similar to the full-length protein (I. Remy & S. W. Michnick, 1999, Proc Natl Acad Sci USA, 96: 5394-5399); in addition, mutations that affect the properties of the intact DHFR protein confer similar properties to the DHFR fragments when they are used in PCA (J. N. Pelletier, F.-X. C.-Valois & S. W. Michnick, 1998, Proc Natl Acad Sci USA 95: 12141-12146). Similarly, fragments of β-lactamase used in PCA are capable of cleavage of cephalosporin substrates with kinetics similar to the intact β-lactamase protein, and mutations that disrupt the molten globule structure of the intact protein improve the enyzymatic properties of the reassembled fragments (A. Galarneau, M. Primeau, L.-E. Trudeau & S. W. Michnick, 2000, Nature Biotechnol. 20: 619-622).

Since the spectral properties of fluorescent proteins are critically dependent upon the orientation and proximity of amino acids relative to the core chromophore, it is not obvious that mutations that affect the spectral properties of an intact fluorescent protein would have the same effect when engineered into fragments of the protein. We reasoned that, if mutations that affect the spectral properties of fluorescent proteins could be engineered into protein-fragment complementation assays, it would be possible to generate a wide variety of PCAs with various spectral properties. Moreover, the availability of different color PCAs would enable the engineering of designer PCAs for a variety of applications in biology and biotechnology.

To demonstrate this principle, we created PCAs based on numerous variants of *A. victoria* green fluorescent protein and tested them by creating fusion constructs with several different human genes known to be involved in protein-protein interactions in mammalian cells. In the first example, fragments were generated for PCA by fragmenting an enhanced green fluorescent protein ("EGFP" in Table 3) in order to create a green fluorescent PCA (GFP PCA). The GFP fragments were then further mutated to create novel fragments having the mutations S65G/V68L/S72A/T203Y which corresponds to the yellow fluorescent protein (YFP) variant named "10C" in Table 2, also referred to as enhanced yellow fluorescent protein ("EYFP") as in Table 3. With intact GFP, the introduction of the S65G/V68L/S72A/T203Y mutations into results in a protein with excitation and emission maxima at 514 nm and 527 nm, respectively, in which the chromophore matures fourfold faster than for the wild type GFP, generating a bright signal for cell biology applications. We sought to determine whether this GFP variant could be used in PCA and to assess the relative intensities of this YFP PCA versus the GFP PCA in cells transiently co-transfected with fragments fused to full-length proteins that had been previously reported to interact in human cells; this analysis is described in detail in Example 1, below.

To demonstrate the utility of the various fragment pairs that are the subject of the invention, we selected three of the fragmentation sites depicted in FIG. 1b and constructed PCAs based on YFP fragments fused to known interacting proteins in various gene/fragment orientations (NN, NC, CN and CC). In Example 2, described below, the results showed that the different fragmentation sites could in fact be used to construct alternative PCAs with good signals vs. background.

In two further examples of the engineering of PCAs based on mutant fragments, we further mutated the YFP fragments in order to determine if mutations shown to enhance the brightness of full-length YFP at physiological temperatures would confer similar properties when engineered into fragments for PCA. First, we engineered two additional mutations, S64L and M153T into YFP[1]. Both the S64L and M153T mutations improve the folding of full-length green fluorescent protein (Tsien, Ann. Rev. Biochem.) and confer enhanced fluorescence to the intact, full-length protein (B P. Cormack et al., Gene 173: 33-38). These mutations are a component of the YFP variant known as SEYFP (see Table 3). In example 3, described in detail below, we directly compared a YFP PCA with the novel SEYFP PCA.

In yet another example of engineering mutant fragments for PCA, we introduced the mutation F46L into fragment 1 of SEYFP, generating novel fragment we designated IFP[1], and we introduced the mutations V163A and S175G into fragment 2 of YFP, generating novel fragment IFP[2]. These mutations are a component of the YFP variant known as SEYFP-F46L ('Venus') in Table 3. The results demonstrate the ability to engineer a highly intense fluorescent PCA (IFP PCA) by engineering mutant fragments of fluorescent proteins.

In a fourth example of the invention, we demonstrated the ability to create PCAs with specific desired spectral properties by creating mutant polypeptide fragments. We created a cyan fluorescent PCA (CFP PCA) by synthesizing fragments with mutations conferring a spectral shift to the blue region. This invention provides fragments for generating a wide spectrum of PCAs through genetic engineering including green, yellow, blue-green, blue, cyan, orange-red and red variants with various intensities and signal maturation characteristics.

In a final example of the invention, we demonstrated multicolor PCAs in which a single fragment of a fluorescent reporter generates different fluorescent colors within the same cell, depending upon the amino acid sequence of the fragment with which it is paired.

Example 1

Creation of Fluorescent Protein-Fragment Complementation Assays and the Generation of Mutant Fragments for PCA We sought to create two PCAs with different spectral properties starting with A. victoria GFP. First, GFP fragments were generated by PCR from a mammalian codon-optimized version of GFP (pCMS-EGFP; Clontech). GFP[1] corresponded to amino acids 1 to 158 and GFP[2] to amino acids 159 to 239 of GFP. Second, fragments encoding a yellow variant of GFP (YFP PCA) were created by introducing the EYFP-specific mutations S65G, S72A into fragment 1 of GFP and the mutation T203Y into fragment 2 of GFP by PCR, resulting in fragments YFP[1] and YFP[2], respectively.

The fragments GFP[1], GFP[2], YFP[1], and YFP[2] were subcloned into a mammalian expression vector (pcDNA3.1Z, Invitrogen), which had previously been modified to incorporate the replication origin (oriP) of the Epstein Barr virus (EBV). The oriP allows episomal replication of these modified vectors in cell lines expressing the EBNA1 gene, such as HEK293E cells (293-EBNA, Invitrogen). Additionally, these vectors still retain the SV40 origin, allowing for episomal expression in cell lines expressing the SV40 large T antigen (e.g. HEK293T, Jurkat or COS) as well.

To test the activity and relative signal intensity of the GFP PCA versus the engineered YFP PCA, PCAs were created for three pairs of proteins that have previously been shown to interact in mammalian cells. These included the self-interaction of the tumor suppressor protein p53 (N. D. Lakin & S. P. Jackson, Oncogene 18: 7644-7655, 1999); the interaction of the papillomavirus E6 protein with p53 (B. A. Werness, A. J. Levine & P. M. Howley, Science 248: 76-79, 1990); and the interaction of the E6 protein with E6AP, a protein that mediates the interaction of E6 with p53 (J. M. Huibregtse, M. Scheffner & P. M. Howley, Mol. Cell. Biol. 13: 775-784, 1993). The full coding sequence for p53, E6 and E6AP was amplified by PCR from a sequence-verified full-length cDNA. The resulting PCR products were cleaned up by vacuum filtration (MultiScreen PCR, Amicon), digested with appropriate restriction enzymes to allow directional cloning, and fused in-frame to either the 5' or 3'-end of GFP[1], YFP[1], GFP[2] or YFP[2] through a flexible linker encoding a 10-amino acid peptide (Gly.Gly.Gly.Gly.Ser)2 (SEQ ID NO:19). The use of a flexible linker between the gene of interest and the reporter fragment assures that the orientation and arrangement of the fusions is optimal to bring the fluorescent protein fragments into close proximity (J. N. Pelletier, F.-X. C.-Valois & S. W. Michnick, 1998, Proc Natl Acad Sci USA 95: 12141-12146). The orientations of the paired constructs was as follows: F1-linker-p53 with F2-linker-p53; F1-linker-E6 with E6AP-linker-F2; and F1-linker-E6 with F2-linker-p53, where F1 and F2 were the fragments of either GFP or YFP. DNAs from recombinant constructs were isolated using Qiagen Turbo BioRobot Prep kits (Qiagen, Chatsworth, Calif.) on a Beckman FX robotic workstation (Beckman Coulter, Fullerton, Calif.). Isolated DNAs were quantitated and then normalized to a concentration of 50 ng/μl.

Twenty-four hours prior to transfection, HEK293E cells were plated (20,000 cells per well) in 24-well plates coated with poly-lysine, then co-transfected with 0.5 micrograms of DNA using Fugene transfection reagent (Roche Diagnostics, Indianapolis, Ind.), as per the manufacturer's recommendations. Following 24 hrs of expression, cells were washed once with PBS and viewed on a Nikon TE-2000 microscope equipped with a HYQ-FITC filter cube (excitation: 460-500 nm; emission: 505-560 nm; dichroic mirror: 505LP). Images were acquired with a CoolSnap HQ CCD camera. FIG. 3 shows the results of fluorescence microscopy of GFP PCA vs.

YFP PCA for the interactions of p53/p53, E6/E6AP and E6/p53. The reconstituted GFP or YFP signal could clearly be seen, and the subcellular localization of the complexes could be determined consistent with their known localizations. However, the YFP PCA signal was visually brighter than the GFP PCA signal for all three protein-protein complexes, demonstrating that the YFP mutations previously shown to enhance the signal intensity of the full-length protein were also effective in enhancing the intensity of the reassembled fragments. Moreover, the excitation and emission maxima of the YFP PCA were nearly identical to that of the intact fluorescent protein YFP 10c (Table 2), suggesting that the complementary fragments are capable of folding and generating a chromophore with substantially the same properties as that generated by the intact protein.

Example 2

Alternative Fragmentation Sites in Fluorescent Proteins

In order to demonstrate that fluorescent protein fragments generated from alternative fragmentation sites—that are the subject of the invention—could be used in PCA, fluorescent protein PCAs based were created for a yellow (YFP) fluorescent protein (see FIG. 4). cDNAs encoding full-length proteins (Pdk2, 14-3-3σ, and the components of the NFκB heterodimer p50 and p65) were fused to either the N- or C-terminus of complementary YFP fragments YFP[1] and YFP[2], corresponding to fragmentation of the full length protein at positions shown in FIG. 1a and FIG. 1b as Gln 157, Lys 158 or Asp 173, where the indicated amino acid residue represents the C-terminus of the N-terminal reporter fragment designated as YFP[1]. Formation of 14-3-3/14-3-3dimers was used to assess the ability of each PCA fragment pair to allow for the detection of protein-protein complexes. Pdk2-YFP[1]/Pdk2-YFP[2] was used as a negative PCA control. HEK293E cells were transiently transfected with 100 ng of each construct pair, and total fluorescence was evaluated 48 hrs later on a Molecular Devices Gemini XS platereader. Each bar represents the mean fluorescence of triplicate measurements, with error bars representing 95% confidence limits. Mock-transfected cells (no DNA or a single DNA construct) are shown in yellow. Various fragment orientations and combinations were tested, since optimal detection of complex formation may be orientation-dependent. In this example, the Lys158 and Asp173 fragmentation sites allowed detection of 14-3-3/14-3-3 complexes in all possible fragment combinations. The Gln156 fragmentation site allowed detection of 14-3-3/14-3-3 complexes in both the NC and CC orientations. Fragment/gene orientations were as follows: NN=14-3-3-YFP[1]/14-3-3-YFP[2]; NC=14-3-3-YFP[1]/YFP[2]-14-3-3; CN=YFP[1]-14-3-3/14-3-3-YFP[2]; CC=YFP[1]-14-3-3/YFP[2]-14-3-3). The results demonstrate the utility of the protein engineering principles that are incorporated into this invention, showing that various fragment pairs are useful for PCA. The compositions that are the subject of the invention include various fragment pairs incorporating a wide range of mutations useful for PCA.

Example 3

Mutant Fragments Generating a Super-Enhanced YFP PCA (SEYFP-PCA) and an Intense Fluorescent PCA (IFP PCA) with Brighter Signals than YFP PCA for Biological Applications To further demonstrate that the spectral properties of a PCA can be influenced by engineering mutant fragments, we first engineered the F64L and M153T mutations of SEYFP into YFP[1] by PCR, creating novel fragment SEYFP[1]. Subcloning was performed as described for Example 1. Fusion constructs were prepared as described above, for the interacting protein kinases MEK and ERK. Specific mutations in each reporter fragment confirmed by sequencing are noted, and are designated relative to wtGFP as in Table 2 and 3.

For quantitative measurements of fluorescence intensity, each well of a 96-well poly-lysine coated plate was seeded with 15,000 HEK293E cells 24 hours prior to transfection. Cells were transfected with 100 ng of DNA in total per well with FuGene transfection reagent, using conditions recommended by the manufacturer. The amount of each fusion construct varied from 50 ng of each construct to as little as 0.1 ng of each construct, with the remaining DNA supplied by an empty 'carrier' vector (e.g. up to 98 ng of carrier DNA for 2 ng total of fusion construct DNA). All transfections were performed in triplicate. Twenty-four or forty-eight hours after transfection, the cells were stained with a 1:300 dilution of Hoescht 33342 (Molecular Probes, Eugene, Oreg.) for 10 minutes, then washed several times with Dulbecco's phosphate buffered saline, then overlaid with a small volume of Hank's Buffered Salt Solution. After a 90 minute incubation at 37° C., mean fluorescence intensity data for each well were acquired on a SpectraMax Gemini XS Plate reader (Molecular Devices), using an excitation wavelength of 485 nm, emission of 527 nm and cutoff of 515 nm. For each sample PCA, mean fluorescence intensity was calculated from triplicate measurements. Relative fold increase in fluorescence was determined by normalizing the mean fluorescence intensity for the test PCA to that of the negative control.

Figure 5:
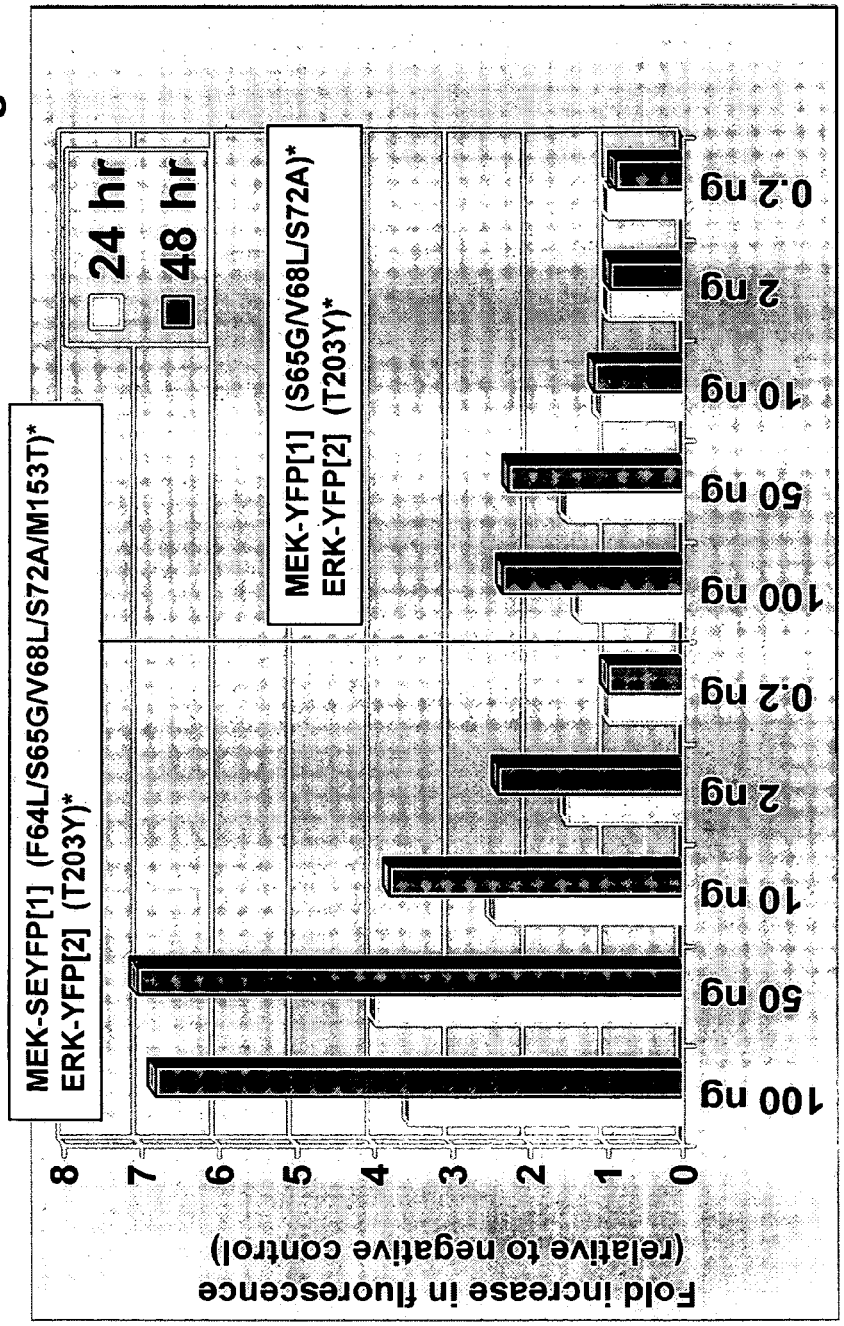
FIG. 5 shows that specific mutations enhance the fluorescent intensities of reassembled fragments, comparing two sequence variants of a YFP PCA that differ by two amino acids; the proteins fused to the complementary fragments are the protein kinases MEK and ERK.

As shown in FIG. 5, the MEK/ERK protein-protein complex could be detected with either of the two fluorescent PCAs. However, the use of SEYFP[1] (F64L and M153T) instead of YFP[1] enhanced the signal intensity two-to four-fold. With this particular mutant YFP PCA (left side of histogram), signal could be readily detected over background with only 2 ng total of 'test' DNA. Moreover, 10 ng DNA for the YFP PCA (right side of histogram) gave a barely detectable signal, whereas the equivalent DNA for the SEYFP PCA gave a signal nearly four times background (left side of histogram). The example demonstrates that mutations known to enhance the intensity of the intact protein confer a similar property on the reassembled fragments.

FIG. 6 shows fluorescence microscopy images of the same PCAs as in FIG. 5, demonstrating that the additional mutations of SEYFP[1] (panel a) enhance the signal intensity as detected by fluorescence microscopy, enabling improved discrimination of the subcellular location of the protein-protein complexes. HEK293E cells were transfected with 5 ng of each fusion construct (plus 90 ng carrier DNA). Images were acquired 48 hrs later using the Discovery-1 automated image acquisition system, using a 20 ms exposure time, and FITC filter set. Protein-protein complexes could also be readily visualized with the YFP PCA (panel b) but were less intense.

Since fragment 1 of these constructs contains all three of the amino acids that form the chromophore in the intact fluorescent protein, we also tested single mutant fragments YFP[L] and YFP[2] to ensure that individual fragments were incapable of generating a fluorescent signal. For panels c and d of FIG. 6, we transfected 50 ng of DNA from a single fusion construct with the indicated mutations. The left hand panel shows the fluorescence image; the right hand panel shows a DAPI stain of the cells, demonstrating that cells were present in the field that was imaged. Neither fragment alone, expressed as a fusion to protein Pdk2, gave a fluorescent signal. In subsequent analyses of over 6000 assays we found that under the experimental conditions we employed, the generation of a fluorescent PCA signal is dependent upon the interacting molecules. This is an important feature of the invention because it demonstrates that we are not tagging proteins with a fluorescent molecule. Rather, we are tagging proteins with polypeptide fragments which themselves are not fluorescent. The fluorescent signal is only generated upon interaction of the molecules to which the reporter fragments are fused. Interaction of the molecules of interest brings the reporter fragments into close proximity, allowing the fragments to fold together into an active structure capable of generating a fluorescent signal.

Figure 7A:
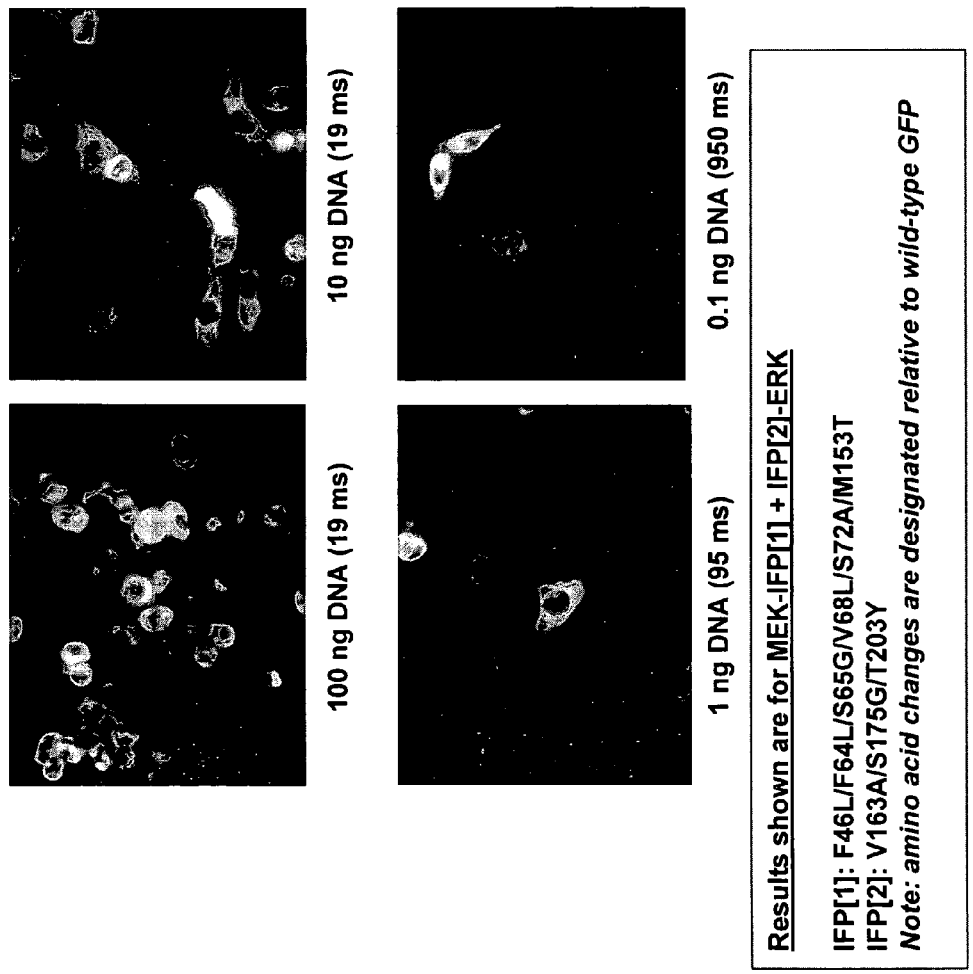
FIGS. 7*a* and 7*b* shows the effect of engineering additional mutations into fragments in order to enhance the fluorescent intensities of the final PCA, creating an intense fluorescent PCA (IFP PCA) and allowing for the detection of protein-protein interactions with low (nanogram to sub-nanogram) quantities of DNA.
Figure 7B:
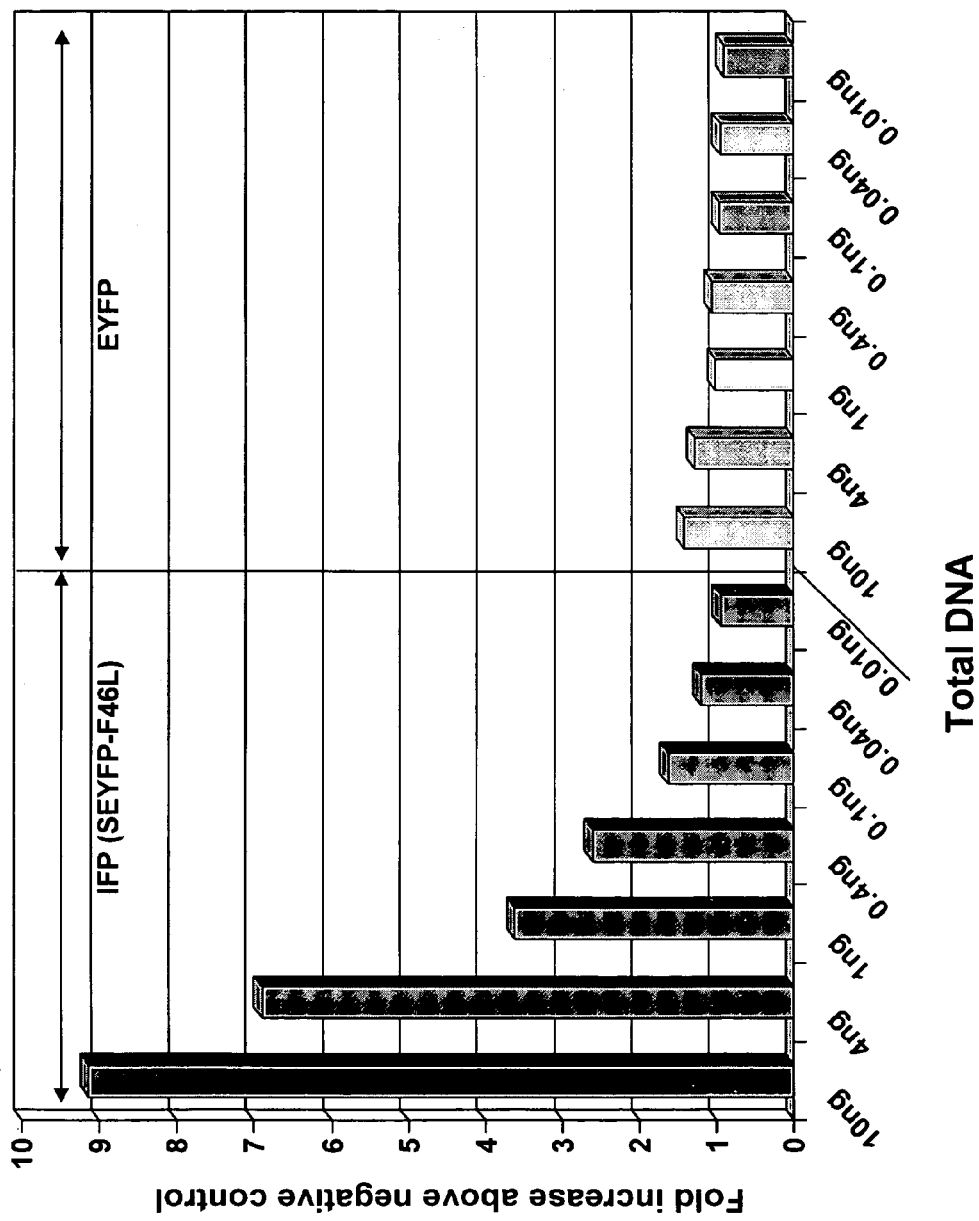

FIGS. 7a and 7b show the creation of yet another novel mutant fluorescent protein PCA allowing even greater sensitivity for biological applications. Mutations were selected based on the YFP variant designated SEYFP-F46L (Venus) in Table 3. These mutations have been shown to accelerate the maturation of the fluorescent signal in the intact protein (T. Nagai et al., 2002, "A variant of yellow fluorescent protein with fast and efficient maturation for cell-biological applications", Nature Biotech. 20: 87-90). PCR mutagenesis was employed to incorporate the additional mutations F46L into SEYFP[1], and V163A and S175G into YFP[2], resulting in novel fragments we designated IFP[1] and IFP[2].

Formation of protein-protein complexes between the MAP kinase signaling proteins, MEK and ERK, was assessed with the novel IFP PCA by fusing MEK1 to the N-terminus of IFP[1] and ERK to the C-terminus of IFP[2]. As shown in FIGS. 7a and 7b, a titration series was performed wherein 100 ng of total DNA was transfected per well, with the amount of DNA contributed by the PCA pair varying from 100 ng down to 100 pg, with the remaining DNA supplied by an empty 'carrier' vector. Fluorescence images were acquired 48 hours later on an SP Nikon fluorescence microscope using a HYQ-FITC filter cube (excitation: 460-500 nm; emission: 505-560 nm; dichroic mirror: 505LP). Images were acquired with a CoolSnap HQ CCD camera with the indicated exposure times (in ms). Total fluorescence for each dilution of the MEK/ERK PCA was also quantified on a fluorescence platereader. Triplicate measurements for each dilution were made, and the mean fluorescence value was normalized to the mean fluorescence of a negative control PCA to determine the fold increase above the negative control, as shown in FIG. 7b. Introduction of the additional mutations into the fragments of YFP greatly enhanced the fluorescent signal which could still be visualized (FIG. 7a) and quantified (FIG. 7b) even at 0.1 ng (100 pg) of DNA. That level of DNA for the IFP PCA produced a significant signal above the negative control (1.5-fold increase). In contrast, to produce an equivalent fluorescence intensity with the YFP PCA, 10 ng DNA was needed.

Figure 8:
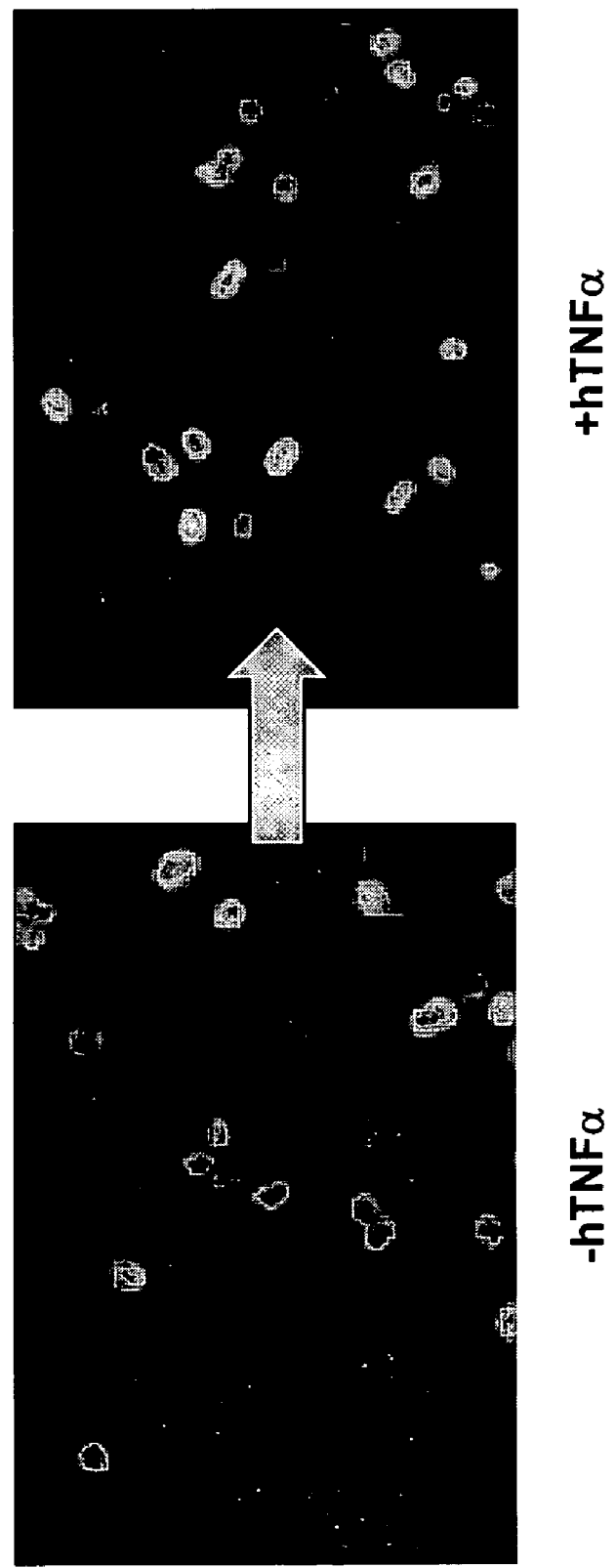
FIG. 8 shows that PCA based on mutant fragments of fluorescent proteins can be used in high-content assays, for example, to detect a change in subcellular localization of protein-protein complexes upon stimulation of living cells by a cytokine as shown here for p65/p50.

The ability to identify the subcellular locations of protein-protein interactions enables high-content screening. For example, the trafficking of proteins within signaling pathways can be seen. For example, we have used this approach with the IFP PCA described above to study the cytokine-induced translocation of the NFκB transcription complex of p65/p50 (FIG. 8). This protein-protein complex translocates from the cytoplasm to the nucleus in live cells in response to tumor necrosis factor. When p65 and p50 are tagged with complementary mutant fragments IFP[1] and IFP[2] respectively in transiently transfected cells, the fluorescent signal can be seen primarily in the cytoplasm in unstimulated cells 48 hours after transfection. Within 30 minutes of treatment of the TNF-responsive HEK cells with TNF-alpha, the fluorescent protein-protein complex moves predominantly to the nucleus.

The above examples demonstrate that mutations can be engineered into fluorescent protein fragments to confer specific desired properties for PCA. Accordingly, we have generated a number of novel fragments of fluorescent proteins incorporating previously described mutations of green fluorescent protein (see Table 2 and Table 3). These mutations have been engineered into fragments generated by fragmentation of fluorescent proteins at the sites depicted in FIG. 1 and described in the above specification. Additionally, we have generated novel fragments at homologous fragmentation sites in coral fluorescent proteins (Table 4), in the monomeric red fluorescent protein (MRFP1) derived from DsRed (Table 5 and Table 6) and a kindling fluorescent protein (KFP1) derived from *Anemonia sulcata* (Table 7 and Table 8). The sequences of the novel fragments are shown in the Appendix prior to the claims of the present invention and are represented as SEQ ID NOS:20-1067 of the Sequence Listing and are the subject of the claimed invention. In general terms we refer to these as "mutant fragments". For the purposes of the invention, a "mutant fragment" is a fragment of a fluorescent protein that has one or more nucleotide or amino acid changes relative to the wild-type cDNA or protein.

Example 4

Spectrally Shifted PCAs

Numerous examples of PCAs generating green fluorescent and yellow fluorescent signals have been described and demonstrated above. The invention described herein allows for PCAs generating a variety of spectral properties depending upon the amino acid sequence of the mutant fragments. In order to further demonstrate this principle, a PCA based on fragments of a cyan fluorescent protein was created to demonstrate blue fluorescence generated by a protein-protein interaction (FIG. 9). Two oligonucleotides corresponding to fragments of CFP were synthesized by Blue Heron Biotechnology (Bothell, Wash.). The resulting fragments were amplified by PCR to attach restriction sites and a flexible 10-aa linker for cloning into a pcDNA3-based expression vector, resulting in vectors containing CFP[1] (encoding aa 1-158 of ECFP) or CFP[2] (encoding aa 159-239 of ECFP) where the CFP had the amino acid sequence shown as ECFP in Table 3. The proteins Pdk2 and 14-3-3a were fused to the N-terminus of CFP[1] and CFP[2], respectively, while the subunits of the NFκB heterodimer p50 and p65 were fused to the C-terminus of the CFP fragments. The construct pairs 14-3-3σ/14-3-3σ, p65/p50 and the Pdk2/Pdk2 negative control were transiently transfected into HEK293T cells, and fluorescence microscopy was performed after 48 hours. Fluorescence images were acquired on an SP Nikon fluorescence microscope using a Chroma CFP filter (excitation: 426-446 nm; emission: 460-500 nm; dichroic mirror: 455LP). Images were acquired with a CoolSnap HQ CCD camera with exposure times of 1-5 sec, as shown in FIG. 8. The results show that mutations causing a spectral shift in the intact fluorescent protein can be engineered into fragments for PCA, resulting in a PCA generating a blue fluorescent signal with utility for biological applications.

Example 5

Multi-Color PCAs

The availability of a suite of fluorescent protein PCAs enables the construction of multi-color PCAs for a variety of biology, biotechnology, drug discovery and diagnostic applications. Such multi-color PCAs are another aspect of the invention.

For example, a 'generic' F2 polypeptide fragment could be combined with multiple distinct F1 mutant fragments in order to detect two, three, four or more bimolecular events simultaneously. This can be achieved by fragmenting a fluorescent protein in such a way that F1 contains all the amino acid residues necessary for chromophore formation when complemented by F2. Two or more mutant fragments of F1 are then created. For example, mutant F1 fragments that are capable of reconstituting either a green, yellow, cyan, blue or red signal can be generated. If F2 is fused to molecule A, and the mutant F1 fragments are fused separately to molecules B, C, D, E and F respectively, the interactions of A with B, A with C, A with D, A with E and A with F can all be tested simultaneously by testing for a fluorescence signal at the 5 different wavelengths that are generated by fragment complementation.

Figure 10:
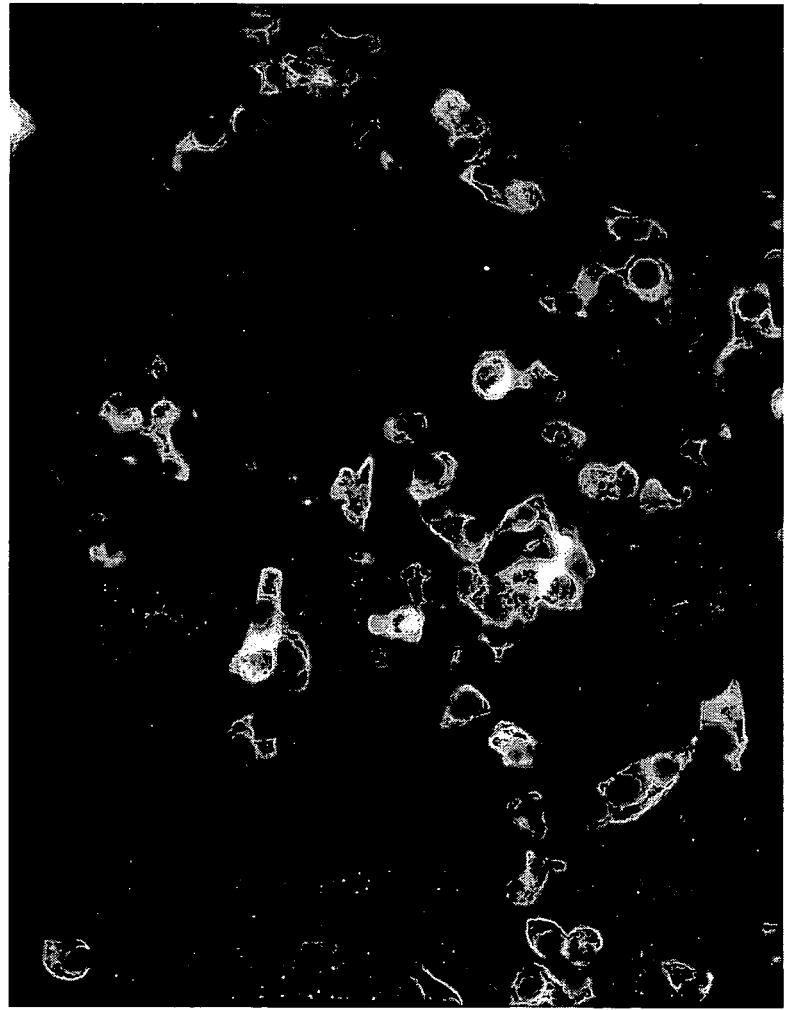

We demonstrated the principles of multi-color PCA in living cells by using the ability of the NFκB p65 subunit to form complexes with the p50 subunit, and also with the protein IkBα as a model system. In resting cells, IkBα binds to NFκB and retains the complex in the cytoplasm. Thus, p65 forms cytoplasmic protein-protein complexes with p50 and also with IκBα We co-transfected HEK293T cells simultaneously with three PCA constructs: CFP[1]-p50; CFP[2]-p65; and IκBα-YFP[1]. Fluorescence images were acquired with an SP Nikon fluorescence microscope using a Chroma CFP filter (excitation: 426-446 nm; emission: 460-500 nm; dichroic mirror: 455LP), and a FITC filter (excitation: 460-500 nm; emission: 505-560 nm; dichroic mirror: 505LP). 16-bit monochrome images were acquired with a CoolSnap HQ CCD camera. CFP and FITC images for each PCA were subsequently pseudocolored and overlaid using Metamorph software (Molecular Devices). If a protein-protein complex forms between p50 and p65, the CFP[l] fragment should complement the CFP[2] fragment, producing blue fluorescence. Alternatively, if a protein-protein complex forms between IkBα and p65, the YFP[1] fragment should complement the CFP[2] fragment, producing a yellow fluorescence. As shown in FIG. 10, both p65/p50 (blue) and IkBα/p65 (yellow) complexes could be detected in the cytoplasm as expected. Cells displaying a lighter yellow (almost white) cytoplasmic staining pattern are expressing both p65/p50 and IkBα/p65 complexes. The ability to construct multi-color PCAs allows for the detection and quantification of multiple distinct protein-protein complexes within the same cells.

Additional Applications of Fluorescent Protein PCAs

The many practical applications of this invention include high-content and high-throughput assays in living cells, cell lysates, or in vitro formats. The applications of the invention include the detection of pathway activation and pathway 'switching' in living cells by agonists, antagonists and inhibitors. The translocation or trafficking of proteins from one subcellular compartment to another can be followed; if protein A initially binds to protein B at the cell membrane and generates a yellow fluorescent signal, and then moves to the cell nucleus and binds to protein C and generates a cyan fluorescent signal, the ratio of cyan to yellow can be used as a detector of the activation of the translocation event. Moreover, there are many applications for fluorescent protein PCAs in diagnostics and nanotechnology. For example, mutant F1 fragments could be bound to a solid surface array, each one as a fusion with a different antibody, which could be used to detect the presence of specific antigens in a sample. The applications of multicolor PCAs include rapid, multicolor diagnostics for biowarfare agents. Such multicolor PCAs are made possible by the novel mutant fragments that are the subject of the present invention.

The cells can be studied in vitro in a variety of formats including tissue culture plates, microtiter plates, or slide formats. The cells harboring PCA constructs can also be studied in vivo. For example, suitable cultured cells stably expressing a particular PCA can be grown as ascites in living animals, or introduced into nude mice to form tumors. Alternative, transgenic mice harboring the PCA constructs can be made. The protein-protein complexes within the animal can then be studied by whole animal imaging systems, for example, those supplied by Xenogen (Alameda, Calif.) or Anti-Cancer (San Diego, Calif.). All the PCAs presented here, and the various intense yellow and red fluorescent PCAs, will be particularly useful for PCA in vivo. In vivo PCA applications include the ability to generate a PCA that responds in vivo to the consumption or injection of a drug by the animal. Applications to pre-clinical drug development include the ability to perform ADME studies (absorption, distribution, metabolism or excretion of a drug) in live animals without sampling blood or urine. For example, if a drug causes an increase or decrease in a specific protein-protein complex within a cell in the live animal, the fluorescent signal can be acquired at various times after drug administration which will allow estimation of the pharmacokinetic and pharmacodynamic properties of the drug in whole animals.

Finally, the availability of a wide range of complementing mutant fragments of fluorescent proteins enables empirical testing for mutant fragment combinations that are particularly useful for PCA. It is likely that this combinatorial feature of PCA will enable the generation of a large number of novel assays with a range of colors, intensities, combinations and physical properties for use in drug screening, target validation, ADME, and diagnostics applications.

The entire contents including the references cited therein of the following patents and publications are incorporated by reference in their entirety for all purposes to the same extent as if each individual patent, patent application or publication were so individually denoted.

| | |
|---|---|
| 6,270,964 | Michnick, et al. |
| 6,294,330 | Michnick, et al. |
| 6,428,951 | Michnick, et al. |
| 5,804,387 | Cormack, et al. |
| 5,625,048 | Tsien, et al. |
| 6,054,321 | Tsien, et al. |
| 6,027,881 | Pavlakis, et al. |
| 6,469,154 | Tsien, et al. |
| 6,066,476 | Tsien, et al. |
| 6,172,188 | Thastrup, et al. |
| 6,968,738 | Anderson, et al. |
| 6,090,919 | Cormack et al. |
| 6,124,128 | Tsien, et al. |
| 6,518,021 | Thastrup, et al. |

Pelletier, J. N., Remy, I. and Michnick, S. W. 1998, Protein-Fragment complementation Assays: a general strategy for the in vivo detection of Protein-Protein Interactions. J. Biomolecular Techniques 10:32-19.

Remy, I., Pelletier, J. N., Galarneau, A. and Michnick, S. W., 2002, Protein Interactions and Library Screening with Protein Fragment Complementation Strategies. in: Protein-protein Interactions: A Molecular Cloning Manual. E. A. Golemis, Editor. Cold Spring Harbor Laboratory Press. Chapter 25, 449-475.

Michnick, S. W., Remy, I., C.-Valois, F. X., Vallee-Belisle, A., Galameau, A. and Pelletier, J. N., 2000, Detection of Protein-Protein Interactions by Protein Fragment Complementation Strategies, Parts A and B (John N. Abelson, Scott D. Emr and Jeremy Thorner, Editors) in: Methods in Enzymology 328: 208-230.

J. N. Pelletier and S. W. Michnick., 1997, A Strategy for Detecting Protein-Protein Interactions in vivo Based on Protein Fragment Complementation. *Protein Engineering*, 10 (Suppl.): 89.

I. Ghosh, A. D. Hamilton and L. Regan, 2000, Antiparallel leucine zipper-directed protein reassembly: application to the green fluorescent protein. J. Am. Chem. Soc 122:5658-5659, 2000

C.-D. Hu et al., 2002, Visualization of interactions among bZIP and Rel family proteins in living cells using bimolecular fluorescence complementation. Molecular Cell 9: 789-798.

Tsien, R. Y., 1998, The Green Fluorescent Protein. in: Annual Reviews of Biochemistry 67: 509-544.

Zhang J., Campbell R. E., Ting A. Y. and Tsien, R. T. (2000) Creating new fluorescent probes for cell biology. Nature Reviews 3: 906-918.

The sequences of the novel fragments are shown in the Appendix below and are represented as SEQ ID NOS:20-

1067 of the Sequence Listing and are the subject of the claimed invention.

Lengthy table referenced here

US08101364-20120124-T00001

Please refer to the end of the specification for access instructions.

While the many forms of the invention herein disclosed constitute presently preferred embodiments, many others are possible and further details of the preferred embodiments and other possible embodiments are not to be construed as limitations. It is understood that the terms used herein are merely descriptive rather than limiting and that various changes many equivalents may be made without departing from the spirit or scope of the claimed invention.

LENGTHY TABLES

The patent contains a lengthy table section. A copy of the table is available in electronic form from the USPTO web site (http://seqdata.uspto.gov/?pageRequest=docDetail&DocID=US08101364B2). An electronic copy of the table will also be available from the USPTO upon request and payment of the fee set forth in 37 CFR 1.19(b)(3).

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US08101364B2). An electronic copy of the "Sequence Listing" will also be available from the USPTO upon request and payment of the fee set forth in 37 CFR 1.19(b)(3).

What is claimed is:

1. A composition comprising complementary fragments of a protein, said fragments generating an optically detectable signal when reassociated.

2. The composition of claim 1 wherein said fragments generate a fluorescent signal when associated.

3. The composition of claim 1 wherein said fragments generate a luminescent signal when associated.

4. The composition of claim 1 wherein said fragments generate a phosphorescent signal when associated.

5. The composition of claim 1 wherein said fragments are derived from a fluorescent protein.

6. The composition of claim 5 wherein said fragments are derived from a mutant fluorescent protein.

7. The composition of claim 6 wherein said complementary fragments differ from the corresponding fragments of the wild-type protein by at least one amino acid.

8. The composition of claim 6 wherein said complementary fragments are selected from the group consisting of: Seq. ID NO: 20 to Seq. ID NO: 1067.

9. The composition of claim 8 wherein said Seq. ID NO: 20 to Seq. ID NO: 1067 are further fused to a separate molecule.

10. A composition comprising complementary fragments of a mutant protein, said fragments generating an optically detectable signal when reassociated, wherein each fragment is fused to a separate molecule.

11. The composition of claim 10 wherein said fragments generate a fluorescent, luminescent or phosphorescent signal when reassociated.

12. The composition of claim 10 wherein said complementary fragments differ from the corresponding fragments of the wild-type protein by at least one amino acid.

13. A Protein fragment complementation assay for the detection of molecular interactions comprising a reassembly of separate inactive fragments from an optically detectable protein wherein reassembly of the fragments is operated by the interaction of molecular domains fused to each fragment, wherein reassembly of the fragments is independent of other molecular processes and wherein said reassembly is detected by means of reconstitution of activity of said optically detectable protein.

14. The assays of claim 13 wherein said fragments generate a fluorescent signal when reassociated.

15. The assays of claim 13 wherein said fragments are derived from a mutant fluorescent protein.

16. A method for detecting biomolecular interactions said method comprising:
 (a) selecting an appropriate optically detectable protein;
 (b) effecting fragmentation of said optically detectable protein such that said fragmentation results in reversible loss of protein function;
 (c) fusing or attaching fragments of said optically detectable protein separately to other molecules;
 (d) reassociating said protein fragments through interactions of the molecules that are fused or attached to said fragments; and
 (e) detecting the resulting optical signal.

17. The method of claim 16 wherein said optically detectable reporter protein is a mutant fluorescent protein.

* * * * *